(12) United States Patent
Cosse et al.

(10) Patent No.: US 9,655,694 B2
(45) Date of Patent: May 23, 2017

(54) ADJUSTABLE-PRESCRIPTION ORTHODONTIC BRACKET ASSEMBLIES

(71) Applicant: Christopher C. Cosse, Shreveport, LA (US)

(72) Inventors: Christopher C. Cosse, Shreveport, LA (US); Calvin N. Corpus, Diamond Bar, CA (US)

(73) Assignee: Christopher C. Cosse, Shreveport, LA (US)

( * ) Notice: Subject to any disclaimer, the term of this patent is extended or adjusted under 35 U.S.C. 154(b) by 164 days.

(21) Appl. No.: 14/559,100

(22) Filed: Dec. 3, 2014

(65) Prior Publication Data

US 2015/0157422 A1 Jun. 11, 2015

Related U.S. Application Data

(60) Provisional application No. 61/913,122, filed on Dec. 6, 2013.

(51) Int. Cl.
*A61C 7/14* (2006.01)
*A61C 7/28* (2006.01)

(52) U.S. Cl.
CPC ............... *A61C 7/14* (2013.01); *A61C 7/287* (2013.01)

(58) Field of Classification Search
CPC ........... A61C 7/14; A61C 7/285; A61C 7/287; A61C 7/148
USPC ....................................... 433/11, 13, 16, 17
See application file for complete search history.

(56) References Cited

U.S. PATENT DOCUMENTS

| | | | |
|---|---|---|---|
| 1,280,628 A | 10/1918 | Angle |
| 1,821,171 A | 9/1931 | Atkinson |
| 3,435,527 A | 4/1969 | Kesling |
| 3,721,005 A | 3/1973 | Cohen |
| 3,748,740 A | 7/1973 | Wildman |
| 3,772,787 A | 11/1973 | Hanson |
| 4,077,126 A | 3/1978 | Pletcher |
| 4,139,945 A | 2/1979 | DiGiulio |
| 4,144,642 A | 3/1979 | Wallshein |
| 4,171,568 A | 10/1979 | Förster |

(Continued)

FOREIGN PATENT DOCUMENTS

WO   WO 2010/105301 A1   9/2010

*Primary Examiner* — Nicholas Lucchesi
(74) *Attorney, Agent, or Firm* — Dascenzo Intellectual Property Law, P.C.; David S. D'Ascenzo

(57) ABSTRACT

Adjustable-prescription orthodontic bracket assemblies are disclosed herein. The orthodontic bracket assemblies include a bracket body, an arcuate core, and a retention structure. The bracket body defines an arcuate receptacle that extends toward a base of the bracket body from a top of the bracket body. The arcuate core is received within the arcuate receptacle and defines an archwire slot. The arcuate receptacle is shaped to retain the arcuate core therein and to permit rotation of the arcuate core therein. The retention structure is configured to selectively retain the arcuate core at a selected rotational orientation with the bracket body. The retention structure is configured to selectively transition between a disengaged configuration, in which the retention structure permits rotation of the arcuate core relative to the bracket body, and an engaged configuration, in which the retention structure retains the arcuate core at the selected rotational orientation.

46 Claims, 13 Drawing Sheets

(56) References Cited

U.S. PATENT DOCUMENTS

| | | |
|---|---|---|
| 4,197,642 A | 4/1980 | Wallshein |
| 4,243,387 A | 1/1981 | Prins |
| 4,248,588 A | 2/1981 | Hanson |
| 4,353,692 A | 10/1982 | Karrakussoglu |
| 4,371,337 A | 2/1983 | Pletcher |
| 4,419,078 A | 12/1983 | Pletcher |
| 4,443,189 A | 4/1984 | Wildman |
| 4,492,573 A | 1/1985 | Hanson |
| 4,496,318 A | 1/1985 | Connelly, Jr. |
| 4,531,911 A | 7/1985 | Creekmore |
| 4,559,012 A | 12/1985 | Pletcher |
| 4,561,844 A | 12/1985 | Bates |
| 4,597,739 A | 7/1986 | Rosenberg |
| 4,614,497 A | 9/1986 | Kurz |
| 4,655,708 A | 4/1987 | Fujita |
| 4,698,017 A | 10/1987 | Hanson |
| 4,712,999 A | 12/1987 | Rosenberg |
| 4,867,678 A | 9/1989 | Parker |
| 4,878,840 A | 11/1989 | Reynolds |
| 5,094,614 A | 3/1992 | Wildman |
| 5,224,858 A | 7/1993 | Hanson |
| 5,302,121 A | 4/1994 | Gagin |
| 5,320,526 A | 6/1994 | Tuneberg |
| 5,322,435 A | 6/1994 | Pletcher |
| 5,466,151 A | 11/1995 | Damon |
| 5,562,444 A | 10/1996 | Heiser et al. |
| 5,586,882 A | 12/1996 | Hanson |
| 5,630,715 A | 5/1997 | Voudouris |
| 5,711,666 A | 1/1998 | Hanson |
| 5,857,850 A | 1/1999 | Voudouris |
| 6,193,508 B1 | 2/2001 | Georgakis |
| 6,302,688 B1 | 10/2001 | Jordan et al. |
| 6,358,045 B1 | 3/2002 | Farzin-Nia et al. |
| 6,582,226 B2 | 6/2003 | Jordan et al. |
| 6,632,088 B2 | 10/2003 | Voudouris |
| 6,655,957 B2 | 12/2003 | Abels et al. |
| 6,659,766 B2 | 12/2003 | Abels et al. |
| 7,025,591 B1 | 4/2006 | Kesling |
| 7,306,458 B1 | 12/2007 | Lu |
| 7,431,586 B1 | 10/2008 | Silverman |
| 7,771,640 B2 | 8/2010 | Cosse |
| 7,819,660 B2 | 10/2010 | Cosse |
| 7,963,768 B2 | 6/2011 | Hilliard |
| 8,272,867 B2 | 9/2012 | Chikami et al. |
| 8,333,586 B2 | 12/2012 | Kantomaa |
| 8,337,198 B2 | 12/2012 | Cosse |
| 8,366,440 B2 | 2/2013 | Bathen et al. |
| 9,198,740 B2 * | 12/2015 | Damon .................. A61C 7/14 |
| 2006/0172247 A1 | 8/2006 | Abels et al. |
| 2008/0293005 A1 | 11/2008 | Rahlis et al. |
| 2011/0183280 A1 | 7/2011 | Cosse et al. |
| 2012/0308952 A1 | 12/2012 | Cosse |
| 2012/0315593 A1 | 12/2012 | Ramos-de-la-Peña et al. |
| 2013/0078595 A1 | 3/2013 | Solano Reina et al. |
| 2014/0205962 A1 | 7/2014 | Damon et al. |
| 2014/0272751 A1 | 9/2014 | Cosse et al. |
| 2014/0370454 A1 * | 12/2014 | Rudman ................ A61C 7/285 433/10 |
| 2016/0175072 A1 * | 6/2016 | Andreiko ............... A61C 7/285 433/11 |
| 2016/0175073 A1 * | 6/2016 | Huang .................... A61C 7/12 433/11 |

* cited by examiner

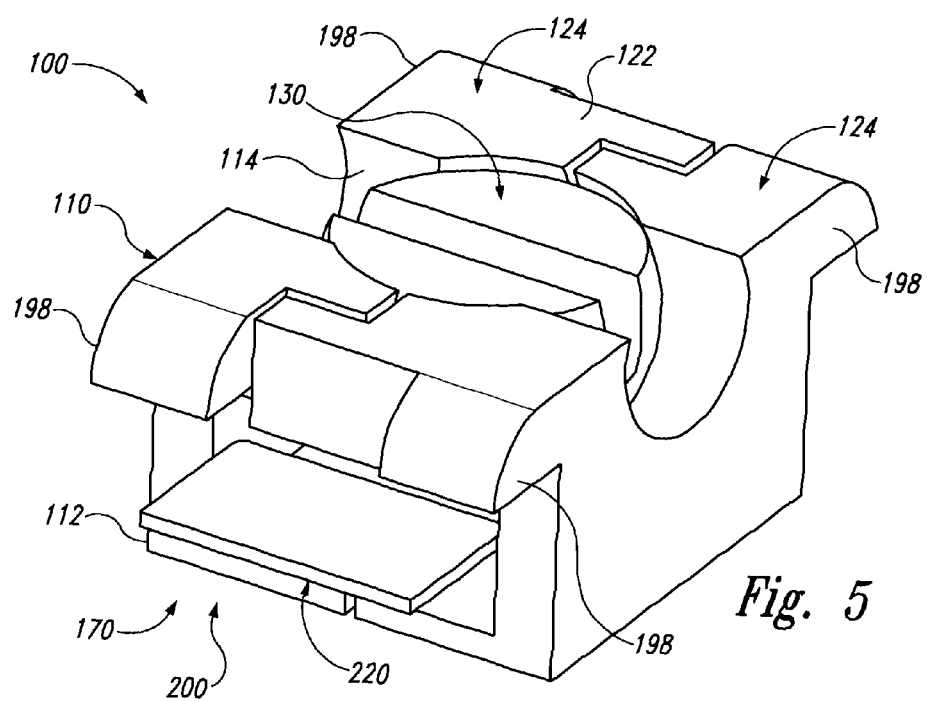
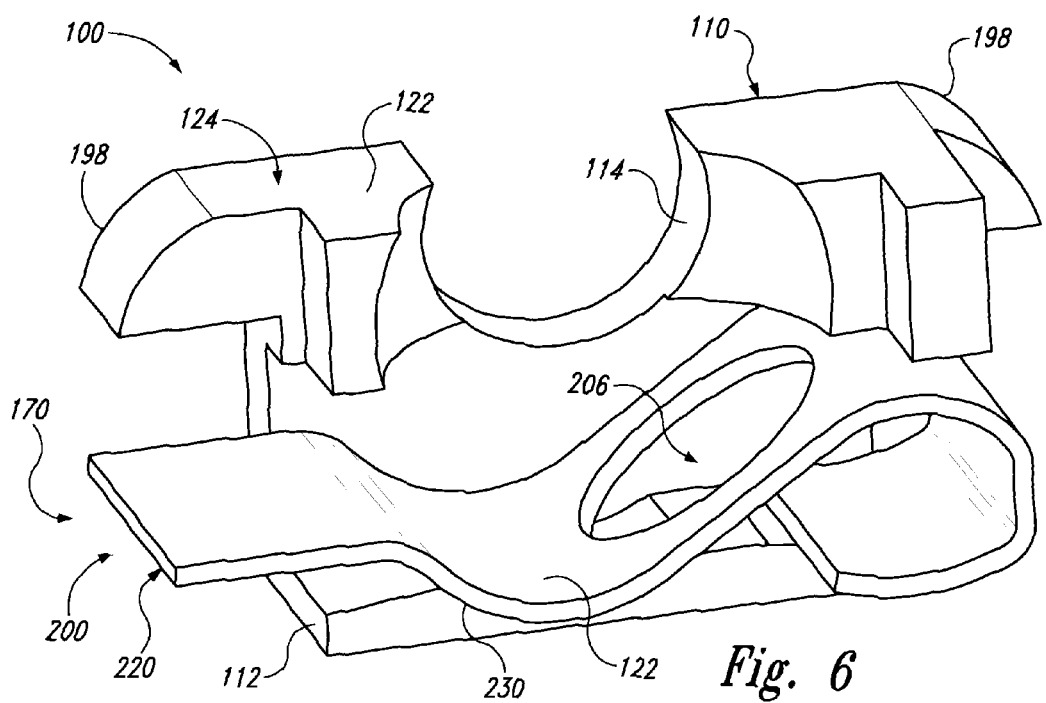

though in some instances brackets may be attached to back surfaces of teeth. Slots in the brackets, which may be referred to herein as archwire slots and/or as archwire passages, are disposed horizontally, or generally horizontally, and are configured to receive an archwire. Traditionally, an archwire is a resilient, curved piece of wire that may be bent and/or twisted prior to installation in the bracket slots, with an archwire typically extending through the slots of all of the orthodontic brackets that are attached to a patient's upper or lower teeth. Engagement between the archwire and the brackets creates corrective, or prescriptive, forces that are directed to the teeth by the orthodontic brackets to urge the teeth into a correct, or desired, alignment, or occlusion.

ADJUSTABLE-PRESCRIPTION ORTHODONTIC BRACKET ASSEMBLIES

RELATED APPLICATION

This application claims priority under 35 U.S.C. §119(e) to U.S. Provisional Patent Application Ser. No. 61/913,122, which was filed on Dec. 6, 2013, and the complete disclosure of which is hereby incorporated by reference.

FIELD OF THE DISCLOSURE

The present disclosure is directed generally to the orthodontic field, and more particularly to adjustable-prescription orthodontic bracket assemblies.

BACKGROUND OF THE DISCLOSURE

Orthodontic brackets typically are small, slotted devices for use during orthodontic treatment. The brackets usually are configured for attachment to front surfaces of teeth, either by directly cementing a bracket to a tooth surface or by bonding the bracket to a metal band that encircles the tooth, though in some instances brackets may be attached to back surfaces of teeth. Slots in the brackets, which may be referred to herein as archwire slots and/or as archwire passages, are disposed horizontally, or generally horizontally, and are configured to receive an archwire. Traditionally, an archwire is a resilient, curved piece of wire that may be bent and/or twisted prior to installation in the bracket slots, with an archwire typically extending through the slots of all of the orthodontic brackets that are attached to a patient's upper or lower teeth. Engagement between the archwire and the brackets creates corrective, or prescriptive, forces that are directed to the teeth by the orthodontic brackets to urge the teeth into a correct, or desired, alignment, or occlusion.

The archwire may be secured in the archwire slot of an orthodontic bracket by a variety of mechanisms, such as depending on the bracket configuration. For example, a "ligating" bracket typically requires a separate fastener, such as a ligature wire or elastic band, which is tied or otherwise positioned around ligating structures, such as tie wings, on the bracket body to secure the archwire in place within the archwire slot of a bracket. A "self-ligating" bracket, on the other hand, typically includes a clamp, gate, or other self-locking mechanism, such as a closeable bracket slot, that allows such a bracket to retain the archwire in the archwire slot without requiring the use of ligatures or other separate fasteners. Ligatures and/or supplemental fasteners or biasing structures also may be used with self-ligating brackets, but they are not required to retain the archwire in the archwire slot.

Regardless of whether the bracket is a self-ligating bracket or whether the bracket requires separate fasteners or ligatures to secure an archwire in the bracket's archwire slot, orthodontic treatment of a patient's teeth typically requires periodic adjustment of the forces that are imparted to the patient's teeth by the installed orthodontic brackets, archwire(s), etc. Adjustments include changing the magnitude and/or direction of the forces that are imparted to the patient's teeth, such as to adjust the degree to which torque, tip, and/or rotational forces are imparted to the patient's teeth to change the angulation, inclination, rotation, height and/or location of the teeth in order to move the teeth toward an optimal occlusion.

As used herein, tipping forces refer to forces applied to the tooth in the mesial-distal direction. Thus, tipping forces may impact angulation. Torsional forces refer to forces applied to the tooth by an archwire that is in torsion within the archwire passage. Thus, torsional forces tend to rotate the tooth in the buccal-lingual or labial-lingual direction and may impact inclination. Rotational forces refer to applied forces that tend to rotate the tooth about its long axis.

Adjustments of some of these forces, including torsional (i.e., torque) forces, typically requires removal of the archwire from the corresponding brackets, along with replacement of the archwire and, in some cases, removal and replacement of one or more brackets. Even with a bracket that permits the applied forces to be adjusted without removal of the bracket from a patient's tooth, fine adjustment of these forces still may be challenging. Thus, there exists a need for improved adjustable-prescription orthodontic brackets.

SUMMARY OF THE DISCLOSURE

Adjustable-prescription orthodontic bracket assemblies are disclosed herein. The orthodontic bracket assemblies include a bracket body, an arcuate core, and a retention structure.

The bracket body defines an arcuate receptacle. The bracket body includes a base, which is configured to be proximal a tooth, and an opposed top, which is configured to be distal the tooth. The arcuate receptacle extends into the bracket body from the top and/or toward the base from the top.

The arcuate core is received within the arcuate receptacle and defines an archwire slot. The archwire slot is sized to receive an archwire during orthodontic use of the bracket assembly. The arcuate receptacle is shaped to retain the arcuate core therein. In addition, the arcuate receptacle also is shaped to permit rotation of the arcuate core therein.

The retention structure is configured to selectively retain the arcuate core at a selected rotational orientation with the bracket body, thereby defining, or establishing, a prescription for the bracket, and thus the prescriptive forces that will be imparted to a patient's tooth during orthodontic use of the bracket assembly. The retention structure is configured to selectively transition between a disengaged configuration, in which the retention structure permits rotation of the arcuate core relative to the bracket body, and an engaged configuration, in which the retention structure retains the arcuate core at the selected rotational orientation.

In some embodiments, the retention structure includes a sliding retention structure. The sliding retention structure is configured to be selectively translated between the engaged configuration and the disengaged configuration. The sliding retention structure extends at least partially between the bracket body and the arcuate core at least when the sliding retention structure is in the engaged configuration.

In some embodiments, the retention structure includes a rotating cam retention structure. The rotating cam retention structure is configured to be selectively rotated between the engaged configuration and the disengaged configuration.

BRIEF DESCRIPTION OF THE DRAWINGS

FIG. 5 is a less schematic view of another example of an orthodontic bracket assembly, according to the present disclosure, that includes a bracket body, an arcuate core, and a sliding retention structure.

FIG. 6 is a partial cross-sectional view of a portion of the orthodontic bracket assembly of FIG. 5.

DETAILED DESCRIPTION AND BEST MODE OF THE DISCLOSURE

Figure 1:
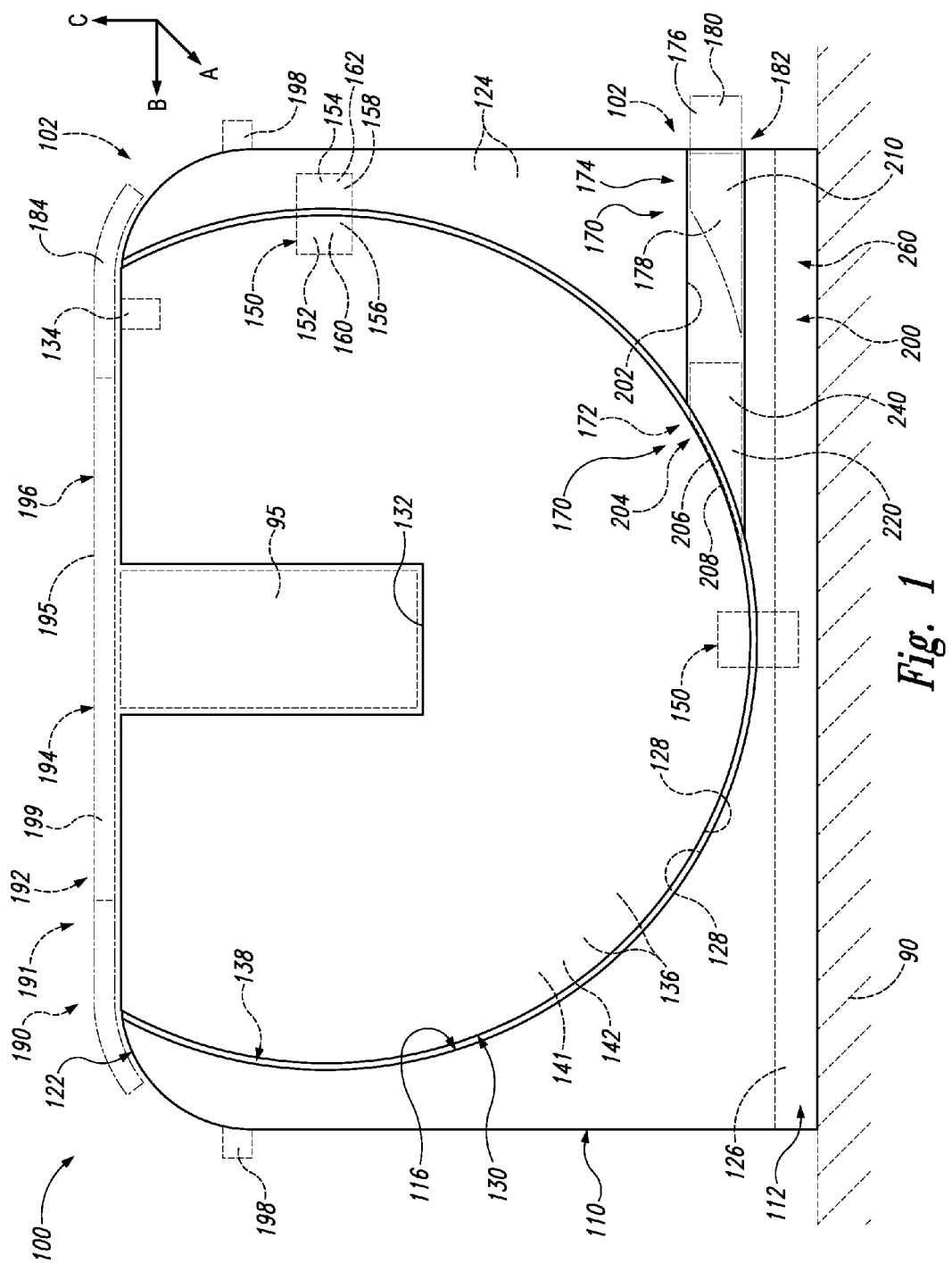
FIG. 1 is a schematic partial cross-sectional view of examples of an orthodontic bracket assembly, according to the present disclosure, that includes a bracket body, an arcuate core, and a retention structure.

FIGS. 1-25 provide examples of orthodontic bracket assemblies 100 according to the present disclosure, components of orthodontic bracket assemblies 100, and/or features of orthodontic bracket assemblies 100. Elements that serve a similar, or at least substantially similar, purpose are labeled with like numbers in each of FIGS. 1-25, and these elements may not be discussed in detail herein with reference to each of FIGS. 1-25. Similarly, all elements may not be labeled in each of FIGS. 1-25, but reference numerals associated therewith may be utilized herein for consistency. Elements, components, and/or features that are discussed herein with reference to one or more of FIGS. 1-25 may be included in and/or utilized with any of FIGS. 1-25 without departing from the scope of the present disclosure.

In general, elements that are likely to be included in a given (i.e., a particular) embodiment are illustrated in solid lines, while elements that are optional to a given embodiment are illustrated in dashed lines. However, elements that are shown in solid lines are not essential to all embodiments, and an element shown in solid lines may be omitted from a particular embodiment without departing from the scope of the present disclosure.

FIG. 1 is a schematic cross-sectional view of examples of an orthodontic bracket assembly 100 according to the present disclosure. Orthodontic bracket assembly 100 also may be referred to herein as a bracket assembly 100 and/or as an assembly 100. Assembly 100 includes a bracket body 110 that defines an arcuate receptacle 116. As illustrated in dashed lines in FIG. 1, assembly 100 may be operatively affixed to a tooth 90, such as via a base 112 of bracket body 110. Base 112 also may be referred to as a bracket base 112. Base 112 may be operatively affixed or otherwise coupled to tooth 90. Base 112 also may be operatively affixed to, coupled to, and/or form a portion of bracket body 110. In some embodiments, base 112 may project beyond the perimeter of the bracket body, in some embodiments, the bracket base is secured to the bracket body during assembly of the bracket assembly, and in some embodiments, the bracket base may be the portion of the bracket body that is closest to the tooth to which the bracket assembly is secured during orthodontic use of the bracket assembly. As used herein, the phrase "orthodontic use" refers to use of a bracket assembly that is secured to a patient's tooth and which contains an archwire operatively secured within the bracket assembly's archwire slot to apply forces to the patient's tooth to alter the relative orientation of the patient's tooth in the patient's mouth.

Assembly 100 also includes an arcuate core 130 that is received within the arcuate receptacle and that defines an archwire slot 132 that is sized to receive an archwire 95 during orthodontic use of the bracket assembly. Assembly 100 further includes a retention structure 170. Arcuate receptacle 116 is shaped to retain arcuate core 130 therein and to permit rotation of the arcuate core about one or more rotational axes. These rotational axes may include and/or be the A-axis, the B-axis, and/or the C-axis of FIG. 1. Retention structure 170 is configured to selectively retain arcuate core 130 at a selected rotational orientation within bracket body 110. As an example, and as discussed in more detail herein, retention structure 170 may be configured to be selectively transitioned between an engaged configuration 172 and a disengaged configuration 174. In the engaged configuration, retention structure 170 retains arcuate core 130 at the selected rotational orientation in any suitable manner. As examples, retention structure 170 may frictionally and/or mechanically retain arcuate core 130 at the selected rotational orientation. In the disengaged configuration, retention structure 170 permits rotation of arcuate core 130 within arcuate receptacle 116 and/or relative to bracket body 110.

Bracket body 110 may include any suitable structure that may define arcuate receptacle 116, may receive arcuate core 130, and/or may be operatively affixed to tooth 90. As discussed, base 112 of bracket body 110 may be proximal to and/or (configured to be) operatively affixed to tooth 90. Bracket body 110 also may include and/or define a top 122. Top 122 may be described as being opposed to base 112, distal base 112, and/or facing away from the patient's tooth 90 to which the bracket body is coupled during orthodontic use of the bracket assembly. Arcuate receptacle 116 may extend from top 122 and/or toward base 112.

Bracket body 110 may be formed and/or defined in any suitable manner and/or may have any suitable configuration. As an example, bracket body 110 may include and/or be a monolithic structure that includes, forms, and/or defines arcuate receptacle 116, base 112 and/or top 122. As another example, bracket body 110 may include a plurality of bracket sections 124 that may be operatively attached and/or affixed to one another and/or that collectively may include, form, and/or define arcuate receptacle 116, base 112, and/or top 122. As a more specific example, bracket body 110 may include at least a first bracket section 124 and a second bracket section 124. The bracket sections 124, such as the first bracket section and the second bracket section, may be operatively affixed to one another and together may define base 112. Alternatively the bracket sections 124 may be operatively affixed to a base section 126 that defines the base. Bracket sections 124 and/or base section 126 may be operatively affixed to one another in any suitable manner. As examples, bracket sections 124 and/or base section 126 may be adhered, melted, alloyed, welded, and/or brazed to one another.

Bracket body 110 may be formed from any suitable material and/or materials. As examples, bracket body 110 may be formed from one or more of a metallic material, a stainless steel, a composite material, and/or a polymeric material.

Assembly 100, bracket body 110, and/or base 112 may be operatively affixed to tooth 90 in any suitable manner. As an example, base 112 may be glued to tooth 90 and/or to a band that encircles tooth 90.

As discussed, retention structure 170 may be configured to frictionally retain arcuate core 130 at the selected rotational orientation relative to bracket body 110 and/or within arcuate receptacle 116. With this in mind, and as illustrated in dashed lines in FIG. 1, bracket body 110 and/or arcuate core 130 may include one or more friction-enhancing regions 128. Friction-enhancing regions 128 may be configured to increase a frictional force between bracket body 110 and arcuate core 130 when retention structure 170 is in engaged configuration 172 and/or to assist retention structure 170 in retaining arcuate core 130 at the selected rotational orientation when the retention structure is in the engaged configuration. Examples of friction-enhancing regions 128 include any suitable roughened surface (or region), high-friction surface (or region), and/or resilient material, surface, or region.

Arcuate receptacle 116 may define any suitable shape and/or may be defined by any suitable surface of bracket body 110. Generally, arcuate receptacle 116 may be shaped to receive arcuate core 130. As an example, the shape of arcuate receptacle 116 may complement a shape of arcuate core 130, the shape of arcuate receptacle 116 may correspond to the shape of arcuate core 130, and/or the shape of arcuate receptacle 116 may be at least substantially similar to at least a portion of the shape of arcuate core 130, such as a portion of arcuate core 130 that contacts bracket body 110. This similar shape between arcuate receptacle 116 and arcuate core 130 may permit arcuate core 130 to be received within and/or to rotate within the arcuate receptacle.

However, arcuate receptacle 116 need not complement the shape of arcuate core 130 in all embodiments. Additionally or alternatively, arcuate receptacle 116 and arcuate core 130 need not both be arcuate. As an example, arcuate receptacle 116 may include and/or define the arcuate shape, while arcuate core 130 may include and/or define any other suitable shape that may be received within and rotate within the arcuate receptacle. Under these conditions, arcuate core 130 also may be referred to herein as a core 130. As another example, arcuate core 130 may include and/or define the arcuate shape, while arcuate receptacle 116 may include and/or define any other suitable shape that may receive and facilitate rotation of the arcuate core. Under these conditions, arcuate receptacle 116 also may be referred to herein as a receptacle 116.

Arcuate receptacle 116 additionally or alternatively may be referred to as an internal chamber 116, arcuate core-receiving cavity 116, a body arcuate receptacle 116, a bracket arcuate receptacle 116, and/or a body compartment 116. Examples of the shape of arcuate receptacle 116 include cylindrical, partial cylindrical, spherical, and/or partial spherical shapes.

Arcuate core 130 may include any suitable structure that defines archwire slot 132, that is sized and/or shaped to be received within arcuate receptacle 116 of bracket body 110, and/or that may rotate about at least one rotational axis while received within bracket body 110. As an example, arcuate core 130 may define a cylindrical shape, an at least substantially cylindrical shape, and/or a partially cylindrical shape. When arcuate core 130 defines the cylindrical shape, the rotational axis may correspond to, be parallel to, or be, a longitudinal axis of the cylindrical shape. Additionally or alternatively, arcuate core 130 may be configured to rotate only about a single rotational axis, and this single rotational axis may correspond to, be parallel to, or be the longitudinal axis of the cylindrical shape.

As another example, arcuate core 130 may define a spherical shape, an at least substantially spherical shape, and/or a partially spherical shape. When arcuate core 130 defines the spherical shape, arcuate core 130 may be configured to rotate about a single rotational axis or a plurality of distinct rotational axes while received within arcuate receptacle 116. As an example, arcuate core 130 may be configured for unconstrained, or at least substantially unconstrained, rotation within arcuate receptacle 116, as discussed in more detail herein.

Figure 2:
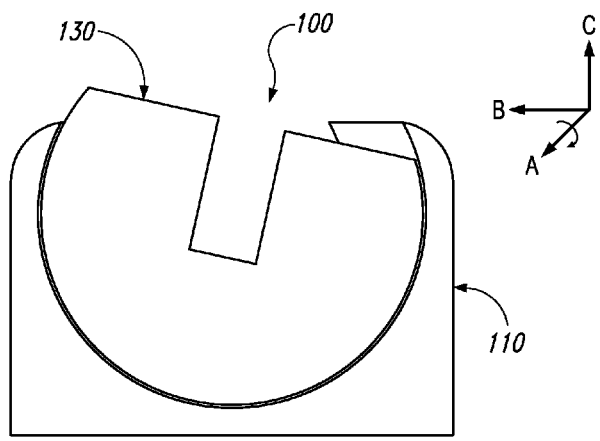
FIG. 2 is a schematic partial cross-sectional view of the orthodontic bracket assembly of FIG. 1 with the arcuate core rotated clockwise about the A-axis.
Figure 3:
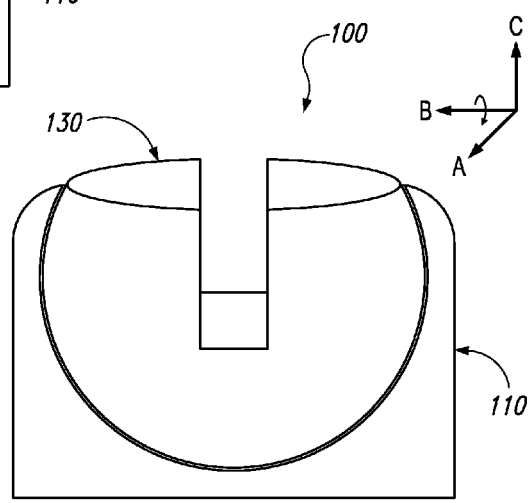
FIG. 3 is a schematic partial cross-sectional view of the orthodontic bracket assembly of FIG. 1 with the arcuate core rotated clockwise about the B-axis.
Figure 4:
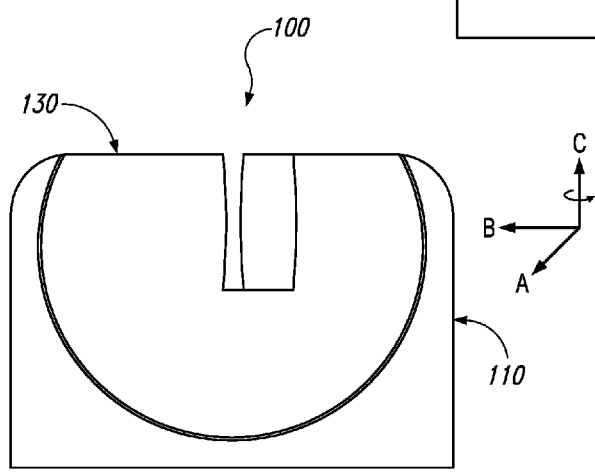
FIG. 4 is a schematic partial cross-sectional view of the orthodontic bracket assembly of FIG. 1 with the arcuate core rotated counterclockwise about the C-axis.

As an example, arcuate core 130 may be configured to rotate about a first rotational axis, such as the A-axis of FIG. 1. This is illustrated in FIG. 2, where arcuate core 130 has been rotated in a clockwise direction about the A-axis (relative to the configuration that is illustrated in FIG. 1). Additionally or alternatively, arcuate core 130 also may be configured to rotate about a second rotational axis, such as the B-axis of FIG. 1. This is illustrated in FIG. 3, where arcuate core 130 has been rotated in a clockwise direction about the B-axis (relative to the configuration that is illustrated in FIG. 1). Additionally or alternatively, arcuate core 130 may be configured to rotate about a third rotational axis, such the C-axis of FIG. 1. This is illustrated in FIG. 4, wherein arcuate core 130 has been rotated in a counterclockwise direction about the C-axis (relative to the configuration that is illustrated in FIG. 1).

Rotational axes A, B, and/or C may define any suitable direction when assembly 100 is operatively affixed to tooth 90. As an example, rotational axis A may extend (at least substantially) in a mesial-distal direction. Under these conditions, rotation of arcuate core 130 about rotational axis A may be utilized to change, adjust, and/or vary torque forces that may be applied to tooth 90 by archwire 95. As another example, rotational axis B may extend (at least substantially) in a gingival-occlusal direction. Under these conditions, rotation of arcuate core 130 about rotational axis B may be utilized to change, adjust, and/or vary rotational forces that may be applied to tooth 90 by archwire 95. As yet another example, rotational axis C may extend (at least substantially) in a buccal-lingual and/or in a labial-lingual direction. Under these conditions, rotation of arcuate core 130 about rotational axis C may be utilized to change, adjust, and/or vary tipping forces that may be applied to tooth 90 by archwire 95. However, rotational axes A, B, and/or C are not required to be orthogonal to one another and/or are not required to align, or align exactly, with the above-described directions. In addition, assembly 100 may be configured to permit arcuate core 130 to be rotated about two, or even three, different rotational axes and/or may permit (substantially) unconstrained rotation of arcuate core 130 within arcuate receptacle 116 over at least a threshold range of rotation when retention structure 170 is in disengaged configuration 174.

Arcuate core 130 may be formed from any suitable material and/or may include any suitable material, or materials, of construction. As examples, arcuate core 130 may include and/or be formed from one or more of a metallic material, a stainless steel, a composite material, and/or a polymeric material.

Arcuate core 130 may be permanently (but adjustably) secured within arcuate receptacle 116 of bracket body 110. It also is within the scope of the present disclosure that arcuate core 130 and/or bracket body 110 may be configured to permit selective removal of the arcuate core from the bracket body and/or replacement of the arcuate core within the bracket body. For example, an arcuate core 130 with a particular construction, archwire slot geometry, and/or archwire slot orientation may be received and replaced with a different arcuate core (i.e., an arcuate core with a different construction, archwire slot geometry, and/or archwire slot orientation) to vary the prescriptive forces that the bracket assembly may impart to a tooth during use of assembly 100.

This may include disassembly of at least a portion of orthodontic bracket assembly 100 to permit removal of the arcuate core from the arcuate receptacle. This disassembly may be accomplished in any suitable manner. As an example, this disassembly may include separation of one or more bracket sections 124 from the bracket body. As another example, this disassembly may include separation of base 112 from the bracket body. As yet another example, this disassembly may include separation of arcuate core 130 into one or more core sections 136. As another example, this disassembly may include removal and/or actuation of a stop, catch, latch, and/or pin that may be associated with orthodontic bracket assembly 100.

As illustrated in dashed lines in FIG. 1, arcuate core 130 further may include and/or define an arcuate core recess 134. Arcuate core recess 134 may be configured, shaped, sized, and/or located to receive an arcuate core adjustment tool. The arcuate core adjustment tool may be configured to be inserted into and/or otherwise coupled to arcuate core recess 134 to enable user inputs, i.e., forces, to be conveyed to the arcuate core via the tool to rotate arcuate core 130, to rotate arcuate core 130 relative to bracket body 110, and/or to rotate arcuate core 130 to the selected rotational orientation. Arcuate core recess 134 additionally or alternatively may be referred to as a tool receiver 134, an arcuate core receiver 134, and/or a socket 134.

Retention structure 170 may include and/or be any suitable structure that may be utilized to selectively retain arcuate core 130 at, or in, the selected rotational orientation within bracket body 110. As an example, retention structure 170 may include and/or be a sliding retention structure 200. As another example, retention structure 170 additionally or alternatively may include and/or be a rotating cam retention structure 260. Examples of sliding retention structures 200 that may be included in assembly 100 of FIGS. 1-4 are illustrated in FIGS. 5-13 and discussed in more detail herein with reference thereto. Examples of rotating cam retention structures 260 that may be included in and/or utilized with assembly 100 of FIGS. 1-4 are illustrated in FIGS. 14-25 and discussed in more detail herein with reference thereto.

Sliding retention structures 200, when present, may be configured to be selectively translated between engaged configuration 172 and disengaged configuration 174. This selective translation may be along a linear, or at least substantially linear, translation path and/or along an arcuate and/or curved translation path. Regardless of the exact shape of the translation path, sliding retention structures 200 may be configured such that a center-of-mass of at least a portion of the sliding retention structure translates upon transitioning between engaged configuration 172 and disengaged configuration 174.

The translation of sliding retention structure 200 may be constrained within (or the sliding retention structure may translate within) a sliding retention structure receptacle 202. The sliding retention structure receptacle may be defined by assembly 100, such as by bracket body 110, base 112, and/or arcuate core 130.

As illustrated in FIG. 1, sliding retention structure 200 may extend at least partially between bracket body 110 (or a portion of the bracket body, such as base 112) and arcuate core 130 at least when the sliding retention structure is in engaged configuration 172. However, the sliding retention structure also may extend between bracket body 110 and arcuate core 130 when the sliding retention structure is in disengaged configuration 174.

Sliding retention structure 200 may be spaced apart from archwire slot 132 and/or may not be utilized to define a portion of archwire slot 132 and/or to retain archwire 95, when present, within archwire slot 132. As an example, arcuate core 130 may extend between sliding retention structure 200 and archwire slot 132.

Sliding retention structure 200 may be shaped and/or configured to operatively engage and/or press against arcuate core 130, such as within a contact area 204 therebetween, when sliding retention structure 200 is in engaged configuration 172. As an example, sliding retention structure 200 may be compressed between arcuate core 130 and bracket body 110 when the sliding retention structure is in the engaged configuration. As another example, sliding retention structure 200 may produce an interference fit between the sliding retention structure and the arcuate core and/or between the sliding retention structure and the bracket body.

The operative engagement between sliding retention structure 200 and arcuate core 130 may cause arcuate core 130 to operatively engage, press against, be urged against, interlock with, and/or generate an interference fit with bracket body 110, such as at an interface region 138 therebetween. This may produce a frictional force within interface region 138 that may retain arcuate core 130 at the selected rotational orientation within bracket body 110.

Sliding retention structure 200 may include a contact region 206. Contact region 206 may be located to define at least a portion, or even all, of contact area 204 between sliding retention structure 200 and arcuate core 130. Additionally or alternatively, contact region 206 may be shaped and/or configured to receive a portion of arcuate core 130 when sliding retention structure 200 is in the engaged configuration. Contact region 206 may include any suitable structure that may be configured to increase contact area 204 and/or to increase the frictional force between sliding retention structure 200 and arcuate core 130 within contact area 204.

As an example, contact region 206 may include and/or be a concave surface profile. As such, contact region 206 may be referred to as a recess, a depression, a receiver, and/or a cavity within the sliding retention structure. The concave surface profile may be shaped to receive arcuate core 130 and/or may have a radius that corresponds to and/or is equal to a radius of a portion of arcuate core 130 that contacts, or is received within, contact region 206.

As another example, contact region 206 may include and/or be a hole, an aperture, and/or a slot within sliding retention structure 200. The hole may be shaped such that sliding retention structure 200 and arcuate core 130 form a line contact therebetween when the sliding retention structure is in the engaged configuration and the arcuate core is received within the hole. For example, a radius of the hole may be less than the radius of the portion of arcuate core 130 that is received within the hole. Examples of the line contact include a circular, an at least substantially circular, an arcuate, and/or an at least substantially arcuate line contact that extends about at least a portion, or even all, of a perimeter of the hole.

Contact region 206 may include a friction-enhancing region 208. Friction-enhancing region 208 may be configured to increase the frictional force between the arcuate core and the sliding retention structure. Examples of the friction-enhancing region include a roughened region, a resilient material, a resilient gasket, and/or a resilient O-ring.

Sliding retention structure 200 also may include a catch 210. Catch 210 may be adapted, configured, designed, sized, and/or shaped to retain sliding retention structure 200 within sliding retention structure receptacle 202 when the sliding retention structure is in disengaged configuration 174, when the sliding retention structure is in engaged configuration 172, and/or regardless of the configuration of the sliding retention structure within the sliding retention structure receptacle.

An example of sliding retention structure 200 is a sliding spring 220, examples of which are illustrated in more detail in FIGS. 5-8 and discussed in more detail herein with reference thereto. When sliding retention structure 200 includes sliding spring 220, sliding retention structure receptacle 202 also may be referred to herein as a sliding spring receptacle 202. Sliding spring 220 may be configured to operatively engage arcuate core 130 and/or to operatively engage arcuate core 130 with bracket body 110 (such as by urging the arcuate core into contact with the bracket body) to retain arcuate core 130 at the selected rotational orientation, as discussed in more detail herein.

Sliding spring 220 may include and/or be any suitable resilient, deformable, and/or compressible structure that may be selectively transitioned between engaged configuration 172 and disengaged configuration 174. As an example, sliding spring 220 may include and/or be a sliding clip, a sliding torsion spring, and/or a sliding flat spring. Sliding spring 220 may have an arcuate shape and/or may be configured to deform upon transitioning between engaged configuration 172 and disengaged configuration 174.

Sliding spring 220 may be formed from any suitable material. As an example, sliding spring 220 may be a metallic sliding spring 220 that is formed from a metallic material, such as a nickel-titanium alloy. As additional examples, sliding spring 220 also may be formed from any suitable resilient material, deformable material, compressible material, and/or polymeric material.

Another example of sliding retention structure 200 is a sliding wedge 240, examples of which are illustrated in FIGS. 9-13 and discussed in more detail herein with reference thereto. When sliding retention structure 200 includes sliding wedge 240, sliding retention structure receptacle 202 also may be referred to herein as a sliding wedge receptacle 202. Sliding wedge 240 may be configured to operatively engage arcuate core 130 and/or to operatively engage arcuate core 130 with bracket body 110 (such as by urging the arcuate core into contact with the bracket body) to retain arcuate core 130 at the selected rotational orientation, as discussed in more detail herein.

Rotating cam retention structures 260, when present, may be configured to be selectively rotated between engaged configuration 172 and disengaged configuration 174. This selective rotation may be about an axis of rotation, which may include, be, and/or be (substantially) parallel to a longitudinal axis of the rotating cam retention structure. Examples of rotating cam retention structures 260 are illustrated in FIGS. 14-25 and are discussed in more detail herein with reference thereto.

As indicated with a dash-dot-dot line in FIG. 1 and discussed in more detail herein, retention structure 170 may include and/or define a projecting portion 178. Projecting portion 178 may be shaped to be received within a retention structure receptacle, such as sliding retention structure receptacle 202. As illustrated in dash-dot-dot lines in FIG. 1 and discussed in more detail herein, retention structure 170 also may include and/or define a tool-receiving portion 180. Tool-receiving portion 180 may be shaped to receive a tool.

As an example, the tool may be configured to be received within tool-receiving portion 180 to transition retention structure 170 between engaged configuration 172 and disengaged configuration 174. This may be accomplished in any suitable manner. As an example, the tool may be translated to transition the retention structure between the engaged configuration and the disengaged configuration. As another example, the tool may be rotated to transition the retention structure between the engaged configuration and the disengaged configuration.

It is within the scope of the present disclosure that another portion of assembly 100, such as bracket body 110, base 112, and/or arcuate core 130, also may include and/or define an assembly tool-engaging portion 102. The assembly tool-engaging portion may be configured to operatively engage the tool when the retention structure is transitioned between the engaged configuration and the disengaged configuration. In such a configuration, the assembly tool-engaging portion may provide additional leverage, a lever point, a pivot point, and/or a fulcrum for actuation of the tool within tool-receiving portion 180 of retention structure 170, thereby changing a direction and/or decreasing a magnitude of force needed to transition the retention structure between the engaged configuration and the disengaged configuration.

Tool-receiving portion 180 may define any suitable shape (or cross-sectional shape). As examples, the tool-receiving portion may define a circular shape, an oblong shape, an oval shape, a rectilinear shape, a rectangular shape, a square shape, and/or a trapezoidal shape. When the tool is configured to be rotated to transition retention structure 170, tool-receiving portion 180 may be shaped and/or sized to permit the rotation and/or may provide clearance for the rotation and/or for contact between the tool and assembly tool-engaging portion 102.

As illustrated in dash-dot-dot lines in FIG. 1 and discussed in more detail herein, retention structure 170 may include an indicator 176. Indicator 176 may include and/or be a visual indicator that may indicate when retention structure 170 is in the engaged configuration and/or in the disengaged configuration. As an example, indicator 176 may be configured to project from bracket body 110 when retention structure 170 is in disengaged configuration 174. This may visually indicate to a wearer of assembly 100 and/or to an orthodontist that is utilizing assembly 100 that retention structure 170 is in the disengaged configuration. As another example, bracket body 110 may include and/or define an indicator recess 182, and indicator 176 may be located within indicator recess 182 when the retention structure is in engaged configuration 172. This may visually indicate to the wearer and/or to the orthodontist that the retention structure is in the engaged configuration.

Regardless of an exact conformation, shape, and/or construction of retention structure 170, retention structures 170 according to the present disclosure may be adapted, configured, designed, and/or constructed to selectively retain arcuate core 130 at the selected rotational orientation within bracket body 110 despite variation in the manufacturing tolerances of bracket body 110, arcuate core 130, and/or retention structure 170. As an example, retention structure 170 may be configured to "take up" and/or otherwise account for the variation in the manufacturing tolerances. As a more specific example, sliding retention structure 200, including sliding spring 220 and/or wedge 240, and/or rotating cam retention structure 260 may be sized and/or shaped to selectively retain arcuate core 130 at the selected rotation orientation within bracket body 110 over a range of clearances therebetween.

As illustrated in dashed lines in FIG. 1, assembly 100 also may include a rotation-directing structure 150. Rotation-directing structure 150 may be configured to permit rotation of arcuate core 130 about a rotational axis (such as the A-axis, the B-axis, and/or the C-axis) and/or to limit rotation of arcuate core 130 about another rotational axis that may be different from a/the rotational axis about which rotation is permitted. The rotational axis may extend in one of a gingival-occlusal direction, in a mesial-distal direction, in a buccal-lingual direction, and/or in a labial-lingual direction, and the rotation-directing structure may restrict rotation about one or more other of these axial directions.

Rotation-directing structure 150 may include any suitable structure that may permit rotation of arcuate core 130 relative to bracket body 110 about the rotational axis (or about a selected rotational axis). Additionally or alternatively, rotation-directing structure 150 also may include any suitable structure that may resist, limit, restrict, and/or block rotation of arcuate core 130 relative to bracket body 110 about the other rotational axes.

As an example, rotation-directing structure 150 may include a groove 152 and a post 154 that is configured to translate within the groove. When rotation-directing structure 150 includes groove 152 and post 154, groove 152 and/or post 154 may be defined by and/or operatively attached to any suitable structure. As an example, one of groove 152 and post 154 may be defined by arcuate core 130, and the other of groove 152 and post 154 may be defined by bracket body 110 and/or by base 112. As another example, and as also discussed herein, arcuate core 130 may be defined by a plurality of arcuate core sections 136. Under these conditions, groove 152 may be defined by a first arcuate core section 136, and post 154 may be defined by a second arcuate core section 136. Groove 152 additionally or alternatively may be referred to as a channel 152, track 152, and/or guide 152. Post 154 additionally or alternatively may be referred to as a projection 154, rib 154, finger 154, and/or pin 154.

As another example, rotation-directing structure 150 may include a hole 156 and a stem 158 that is configured to rotate within the hole. When rotation-directing structure 150 includes hole 156 and stem 158, hole 156 and/or stem 158 may be defined by and/or operatively attached to any suitable structure. As an example, one of hole 156 and stem 158 may be defined by arcuate core 130, and the other of hole 156 and stem 158 may be defined by bracket body 110 and/or by base 112, when present. As another example, and when arcuate core 130 is defined by the plurality of arcuate core sections 136, hole 156 may be defined by the first arcuate core section 136 and stem 158 may be defined by the second arcuate core section 136.

As yet another example, rotation-directing structure 150 may include a rib 160. Rib 160 may project from one of arcuate core 130 and bracket body 110 and may be configured to press against a guiding surface 162 to direct, control, and/or regulate rotation of arcuate core 130 within bracket body 110.

As illustrated in dashed lines in FIG. 1, bracket assembly 100 further may include a ligating structure 190, which may be configured to selectively retain archwire 95, when present, within archwire slot 132. Ligating structure 190 may be operatively affixed and/or attached to arcuate core 130, as illustrated in dashed lines in FIG. 1. As illustrated, the ligating structure obstructs the opening of archwire slot 132 and thereby restricts insertion or removal of the archwire through the opening when the ligating structure is in such an operative position. Additionally or alternatively, ligating structure 190 also may be operatively affixed and/or attached to bracket body 110, as illustrated in dash-dot lines.

Figure 9:
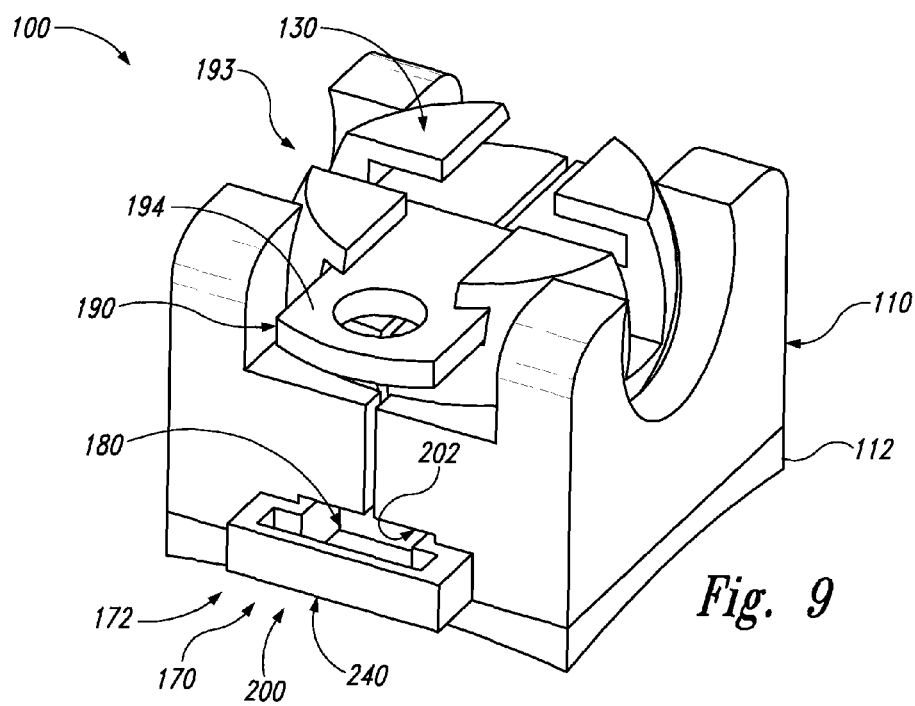
FIG. 9 is a less schematic view of another example of an orthodontic bracket assembly, according to the present disclosure, that includes a bracket body, an arcuate core, and a sliding retention structure.

Ligating structure 190 may include and/or be any suitable structure that may be configured to retain archwire 95 within archwire slot 132. As an example, orthodontic bracket assembly 100 may include and/or be a self-ligating orthodontic bracket assembly 100. Under these conditions, ligating structure 190 may be a closure 194 and/or a gate 194 that forms a portion of orthodontic bracket assembly 100. Gate 194 may be configured to transition between an open configuration 193 (as illustrated in FIG. 9), in which archwire 95 is not retained within archwire slot 132, and a closed configuration 191, in which archwire 95 is retained within the archwire slot. This may include transitioning and/or translating within a ligating structure receptacle 192 that may be defined by assembly 100 and/or by bracket body 110 and/or arcuate core 130 thereof. Expressed in slightly different terms, archwire slot 132 defines a longitudinal axis that is bounded on three sides by arcuate core 130, with gate 194 selectively bounding the archwire slot on a fourth side to form a closed perimeter in a direction transverse to the longitudinal axis when the gate is in the closed configuration. When the gate is in the open configuration, the archwire may be removed from the archwire slot, such as by moving the archwire out of the slot in a direction perpendicular to the longitudinal axis.

Additionally or alternatively, orthodontic bracket assembly 100 may not be a self-ligating orthodontic bracket assembly 100. Under these conditions, ligating structure 190 may include and/or be a ligature 196 that may be operatively affixed to orthodontic bracket assembly 100, such as via one or more ligature-receiving structures 198, to secure the archwire within the archwire slot. Examples of ligature 196 include any suitable wire, band, and/or rubber (elastomeric) band. Examples of ligature-receiving structures 198 include, but are not limited to, tie wings, hooks, grooves, recesses, and/or projections. Ligatures 196 and/or ligature-receiving structures 198 also may be utilized with self-ligating bracket assemblies, including those disclosed, illustrated, and/or incorporated herein.

Regardless of the exact configuration, ligating structure 190 may include and/or be an active ligating structure or a passive ligating structure. When ligating structure 190 is a passive ligating structure, the ligating structure may not actively press against archwire 95, when present. When ligating structure 190 is an active ligating structure, the ligating structure further may include a biasing mechanism 199 that is configured to provide a compressive force to archwire 95, when present.

When assembly 100 is self-ligating orthodontic bracket assembly 100, ligating structure 190 further may define a ligating structure tool-receiving portion 195 that may be shaped to receive a tool. Ligating structure tool-receiving portion 195 may define any suitable shape, examples of which are discussed herein with reference to tool-receiving portion 180.

When the tool is received within ligating structure tool-receiving portion 195, the tool may be translated to translate ligating structure 190, to translate ligating structure 190 within ligating structure receptacle 192, and/or to transition ligating structure 190 between the closed configuration and the open configuration. Additionally or alternatively, the tool also may be rotated to translate ligating structure 190, to translate ligating structure 190 within ligating structure receptacle 192, and/or to transition ligating structure 190 between the closed configuration and the open configuration. When the tool is rotated, assembly 100 further may define tool-engaging portion 102, which is discussed in more detail herein.

When orthodontic bracket assembly 100 includes ligating structure 190, retention structure 170 also may include and/or be a ligating structure extension 184. Ligating structure extension 184 may be at least partially defined by ligating structure 190 and may be configured to operatively interlock arcuate core 130 with bracket body 110 and/or with base 112 (when present), thereby restricting rotation of arcuate core 130 and/or retaining arcuate core 130 at the selected rotational orientation.

As discussed, orthodontic bracket assembly 100 includes rotation-directing structure 150 and retention structure 170.

It is within the scope of the present disclosure that assembly 100 may include a plurality of rotation-directing structures 150.

As an example, assembly 100 may include a first rotation-directing structure 150 that is configured to permit rotation of arcuate core 130 about a first rotational axis and/or to resist rotation of arcuate core 130 about one or more other rotational axes. In addition, assembly 100 also may include a second rotation-directing structure 150 that is configured to permit rotation of arcuate core 130 about a second rotational axis and/or to resist rotation of arcuate core 130 about one or more other rotational axes. The second rotational axis may be different from, or even perpendicular to, the first rotational axis.

As a more specific example, and as discussed in more detail herein, arcuate core 130 may include a plurality of arcuate core sections 136 that are secured together to collectively form arcuate core 130. For example, the plurality of arcuate core sections 136 may include at least a first arcuate core section 141 and a second arcuate core section 142. Under these conditions, first rotation-directing structure 150 may be configured to permit the first arcuate core section to rotate relative to bracket body 110 about the first rotational axis, and second rotation-directing structure 150 may be configured to permit the second arcuate core section to rotate relative to the first arcuate core section about the second rotational axis. The second rotation-directing structure may be at least partially defined by the first arcuate core section and by the second arcuate core section.

Bracket assembly 100 also may include a corresponding plurality of retention structures 170. As an example, a first retention structure 170 may be configured to selectively retain arcuate core 130 in a first selected rotational orientation about the first rotational axis, and a second retention structure 170 may be configured to selectively retain arcuate core 130 in a second selected rotational orientation about the second rotational axis.

Additional examples of orthodontic bracket assemblies, bracket bodies, arcuate cores, archwire slots, accessories, constructions, ligatures, gates, methods of use, etc. are disclosed in U.S. Pat. Nos. 3,772,787, 4,197,642, 4,248,588, 4,443,189, 4,492,573, 4,698,017, 5,094,614, 5,466,151, 5,562,444, 5,586,882, 5,630,715, and 7,819,660, and U.S. Patent Application Publication Nos. 2011/0183280, 2012/0308952, and 2014/0272751, the complete disclosures of which are incorporated by reference.

FIGS. 5-25 provide less schematic examples of orthodontic bracket assemblies 100, components of assemblies 100, and/or features of assemblies 100 according to the present disclosure. The orthodontic bracket assemblies of FIGS. 5-25 may include and/or be more detailed examples of assemblies 100 of FIGS. 1-4, and any of the structures, functions, and/or features discussed herein with reference to assemblies 100 of FIGS. 1-4 may be included in and/or utilized with assemblies 100 of FIGS. 5-25 without departing from the scope of the present disclosure. Similarly, any of the structures, functions, and/or features discussed herein with reference to assemblies 100 of FIGS. 5-25 may be included in and/or utilized with assemblies 100 of FIGS. 1-4.

Figure 7:
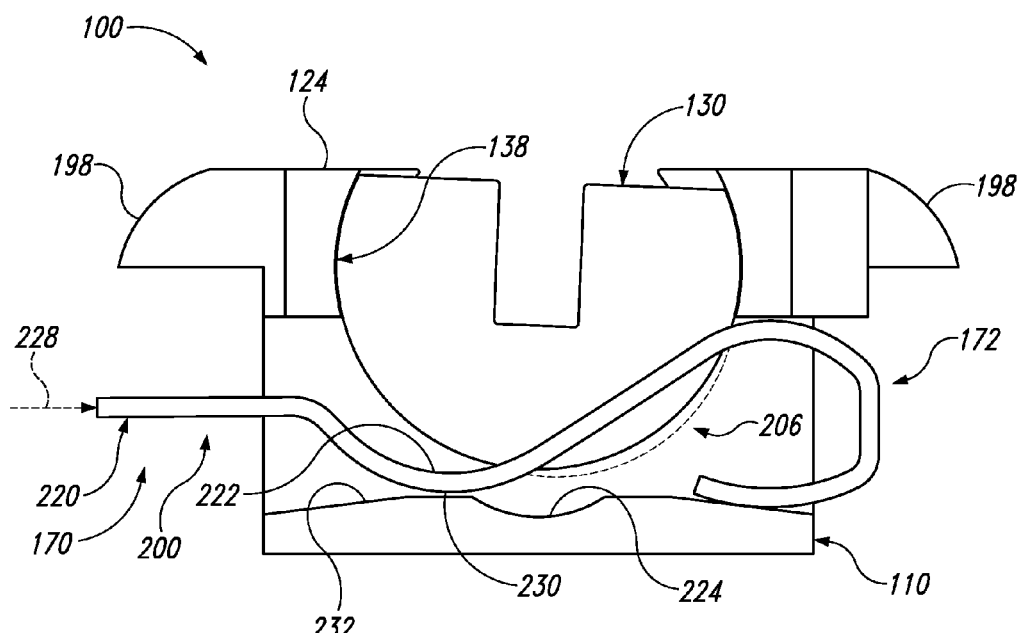
FIG. 7 is a side partial cross-sectional view of a portion of the orthodontic bracket assembly of FIG. 5 illustrating the sliding retention structure in an engaged configuration.
Figure 8:
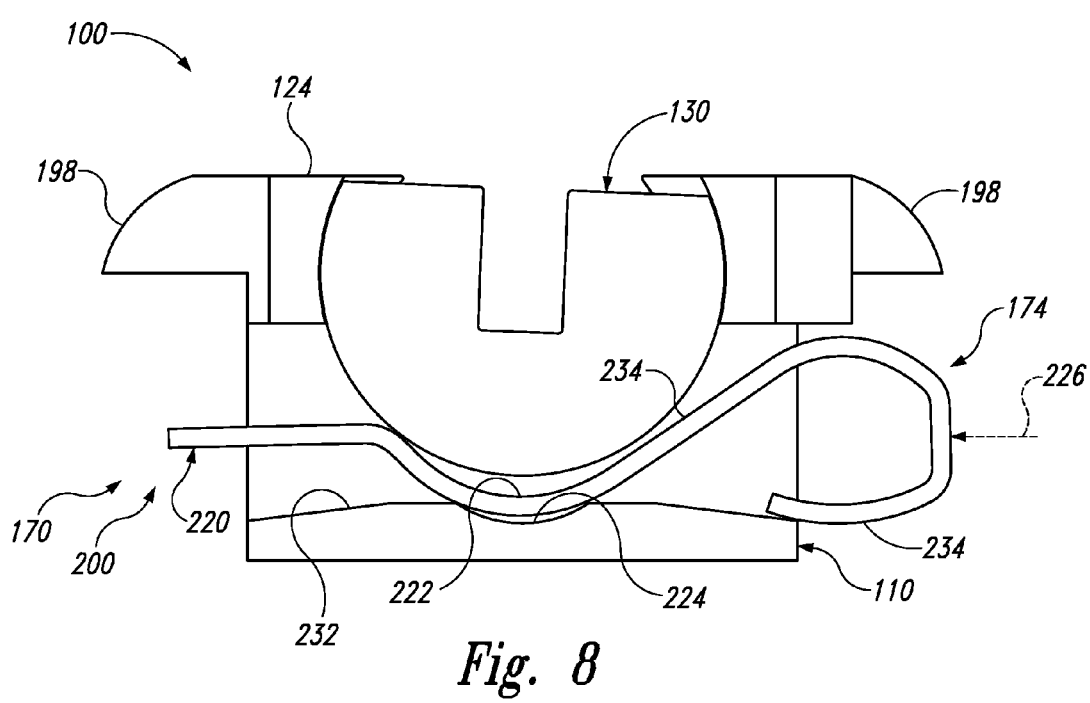
FIG. 8 is a side partial cross-sectional view of a portion of the orthodontic bracket assembly of FIG. 5 illustrating the sliding retention structure in a disengaged configuration.

FIG. 5 is a less schematic view of additional examples of orthodontic bracket assemblies 100, according to the present disclosure, that include a bracket body 110, an arcuate core 130, and a retention structure 170 in the form of a sliding retention structure 200. FIG. 6 is a view of a portion of the orthodontic bracket assemblies of FIG. 5. FIG. 7 is a side view of a portion of the orthodontic bracket assemblies of FIG. 5 illustrating the sliding retention structure in an engaged configuration 172, and FIG. 8 is a side view of a portion of the orthodontic bracket assemblies of FIG. 5 illustrating the sliding retention structure in a disengaged configuration 174. Sliding retention structure 200 of FIGS. 5-8 includes a sliding spring 220.

Sliding spring 220 may be configured to slide and/or translate to transition between the engaged configuration and the disengaged configuration. This is illustrated in FIGS. 7-8. Sliding and/or translation of sliding spring 220 between the engaged configuration and the disengaged configuration may include deformation of one or more deformation regions 234 of the sliding spring.

In FIG. 7, sliding spring 220 is in engaged configuration 172. When the sliding spring is in the engaged configuration, the sliding spring presses against arcuate core 130 and urges the arcuate core into contact with bracket body 110 within an interface region 138 therebetween. In the engaged configuration, frictional forces between arcuate core 130 and bracket body 110 and/or between arcuate core 130 and sliding spring 220 retain the arcuate core in a given, or selected, rotational orientation within bracket body 110.

In FIG. 8, sliding spring 220 is in disengaged configuration 174. When the sliding spring is in the disengaged configuration, the sliding spring does not press against arcuate core 130, does not urge the arcuate core into contact with bracket body 110, does not press against arcuate core 130 with sufficient force to retain the arcuate core in the selected rotational orientation, and/or does not urge the arcuate core into contact with the bracket body with sufficient force to retain the arcuate core in the selected rotational orientation, thereby permitting and/or facilitating adjustment of the angular orientation of the arcuate core within the bracket body.

As illustrated in FIGS. 7-8, sliding spring 220 includes a relief region 222. Relief region 222 may be shaped to provide clearance for rotation of arcuate core 130 when the sliding spring is in disengaged configuration 172, as illustrated in FIG. 8. As shown, relief region 222 may include and/or be a concave (or other) portion of the sliding spring that may provide clearance for rotation of the arcuate core when the sliding spring is oriented such that the relief region is aligned with the arcuate core. When relief region 222 is aligned with arcuate core 130, sliding spring 220 may not press against the arcuate core and/or may press against the arcuate core with a force that is low enough in magnitude to permit and/or facilitate adjustment of the rotational orientation of the arcuate core. Stated another way, a magnitude of a force that is applied to arcuate core 130 by sliding spring 220 when the sliding spring is in the disengaged configuration may be less than a magnitude of a force that is applied to the arcuate core by the sliding spring when the sliding spring is in the engaged configuration.

As illustrated most clearly in FIGS. 7-8, bracket body 110 may have, include, and/or define a detent 224. Detent 224 also may be referred to herein as a concave region 224 and/or as a clearance region 224 and may be sized, located, and/or shaped to receive relief region 222 of sliding spring 220 (or a portion of the sliding spring that defines the relief region) when the sliding spring is in disengaged configuration 174. This is illustrated in FIG. 8. Relief region 222 and detent 224 together may be shaped to bias sliding spring 220 toward and/or into disengaged configuration 174 when the relief region is received within the detent. As an example, and as illustrated in FIG. 8, sliding spring 220 may be biased to extend and/or urge relief region 222 into detent 224 when the sliding spring is in the disengaged configuration. Thus, sliding spring 220 may be adapted, configured, shaped, and/or biased to remain in the disengaged configuration unless urged from the disengaged configuration, such as via application of an engaging force 226 thereto.

Application of engaging force 226 to sliding spring 220 may cause the sliding spring to automatically transition to engaged configuration 172 of FIG. 7. As an example, application of engaging force 226 may urge relief region 222 from detent 224. Subsequent to the relief region being urged from the detent, the sliding spring may automatically transition to the engaged configuration.

Once in engaged configuration 172, the sliding spring may be shaped and/or biased to remain in the engaged configuration unless urged therefrom, such as via application of a disengaging force 228 thereto (as illustrated in FIG. 7). As an example, sliding spring 220 may include a bias region 230 that is shaped to retain the sliding spring in the engaged configuration unless urged therefrom. In FIGS. 6-7, bias region 230 corresponds to relief region 222; however, this is not required.

As another example, bracket body 110 may include and/or define a transition structure 232, as illustrated in FIGS. 7-8. Transition structure 232 may include and/or be an angled and/or sloped region that may interact with sliding spring 220. As an example, transition structure 232 and bias region 230 together may be shaped to bias sliding spring 220 toward the engaged configuration.

FIGS. 5-8 also provide less schematic examples of structures and/or features of assemblies 100, bracket bodies 110, arcuate cores 130, and/or retention structures 170 according to the present disclosure that are discussed herein with reference to FIGS. 1-4. As an example, bracket bodies 110 of FIGS. 5-8 may include one or more ligature-receiving structures 198 that project from the bracket body to provide a mount, or anchor, for a wire, elastic, or other ligature. As another example, and as labelled in FIGS. 5-6, bracket bodies 110 also may include and/or define one or more clearance regions 114. Clearance regions 114 may be shaped to permit the archwire to pass therethrough for a variety of rotational orientations of arcuate core 130. As yet another example, bracket bodies 110 may include a plurality of bracket sections 124 that are secured together during assembly of the bracket body.

As another example, sliding retention structures 200 of FIGS. 5-8 include and/or define a contact region 206, as illustrated in FIG. 6. In FIG. 6, contact region 206 includes a hole within sliding spring 220, and this hole is sized to receive a portion of arcuate core 130, as illustrated in FIG. 7. Additionally or alternatively, and as illustrated in dashed lines in FIG. 7, contact region 206 also may include and/or be a concave region of sliding spring 220 that is sized to receive the portion of arcuate core 130.

Figure 10:
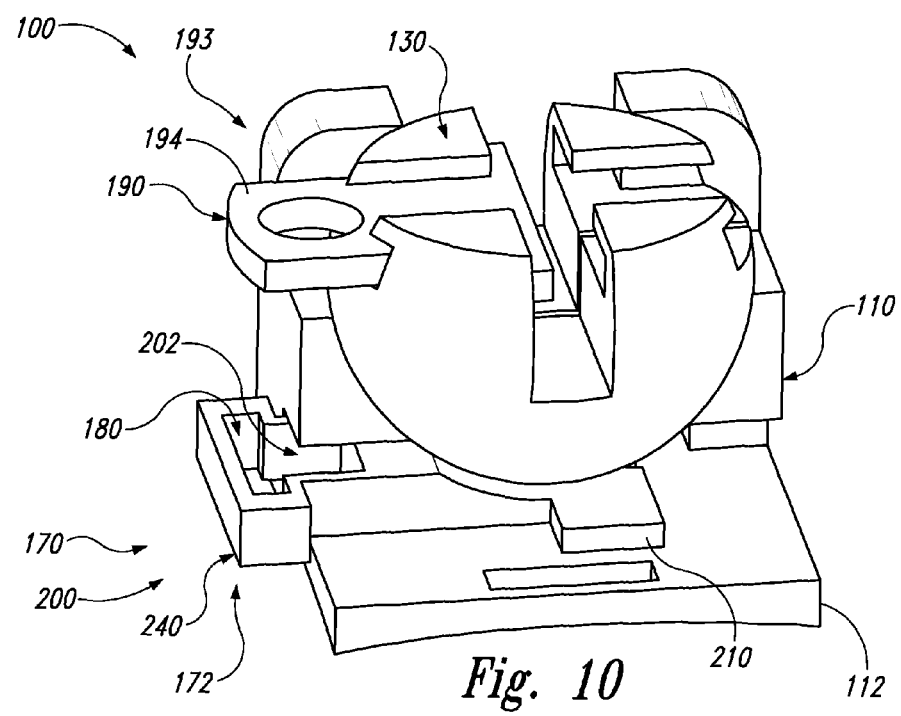
FIG. 10 is a fragmentary view of a portion of the orthodontic bracket assembly of FIG. 9.
Figure 11:
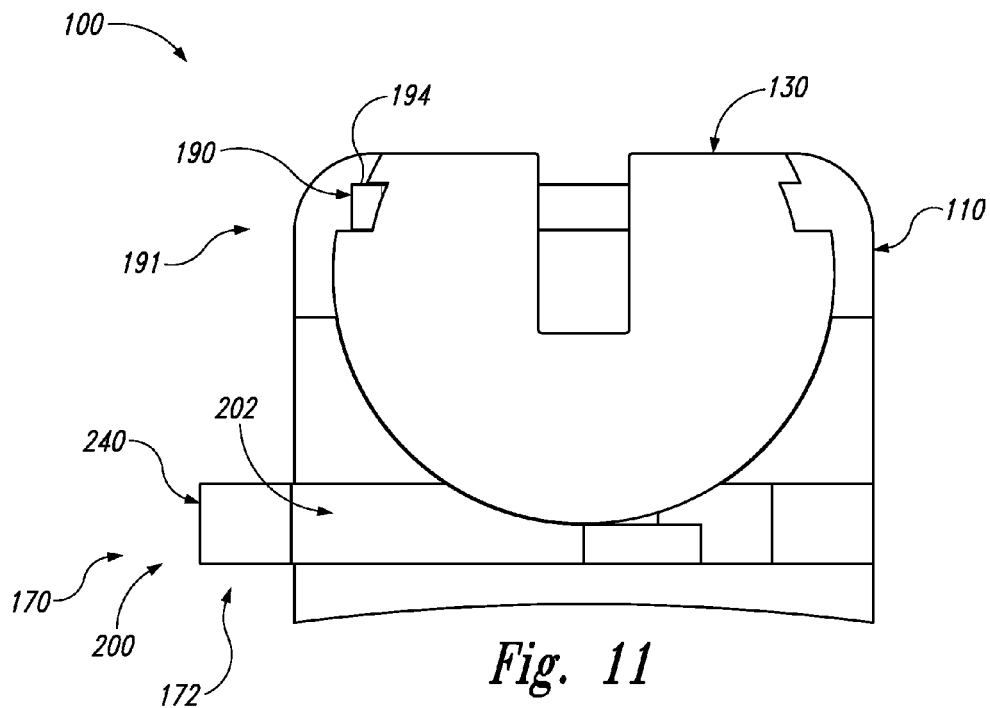
FIG. 11 is a fragmentary side view of a portion of the orthodontic bracket assembly of FIG. 9 illustrating the sliding retention structure in an engaged configuration.

FIG. 9 is a less schematic view of another example of orthodontic bracket assemblies 100, according to the present disclosure, that include a bracket body 110, an arcuate core 130, and a retention structure 170 in the form of a sliding retention structure 200. FIG. 10 is a view of a portion of the orthodontic bracket assemblies of FIG. 9. FIG. 11 is a side view of a portion of the orthodontic bracket assemblies of FIG. 9 illustrating the sliding retention structure in an engaged configuration 172, and FIG. 12 is a side view of a portion of the orthodontic bracket assemblies of FIG. 9 illustrating the sliding retention structure in a disengaged configuration 174.

Figure 12:
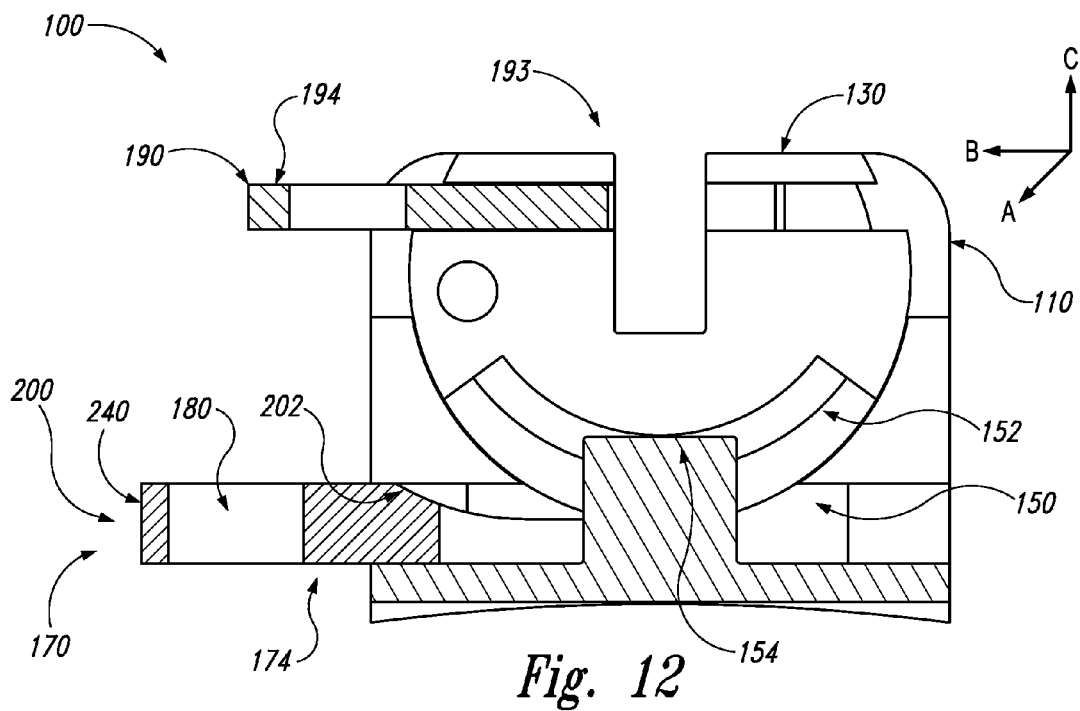
FIG. 12 is a side partial cross-sectional view of a portion of the orthodontic bracket assembly of FIG. 9 illustrating the sliding retention structure in a disengaged configuration.
Figure 13:
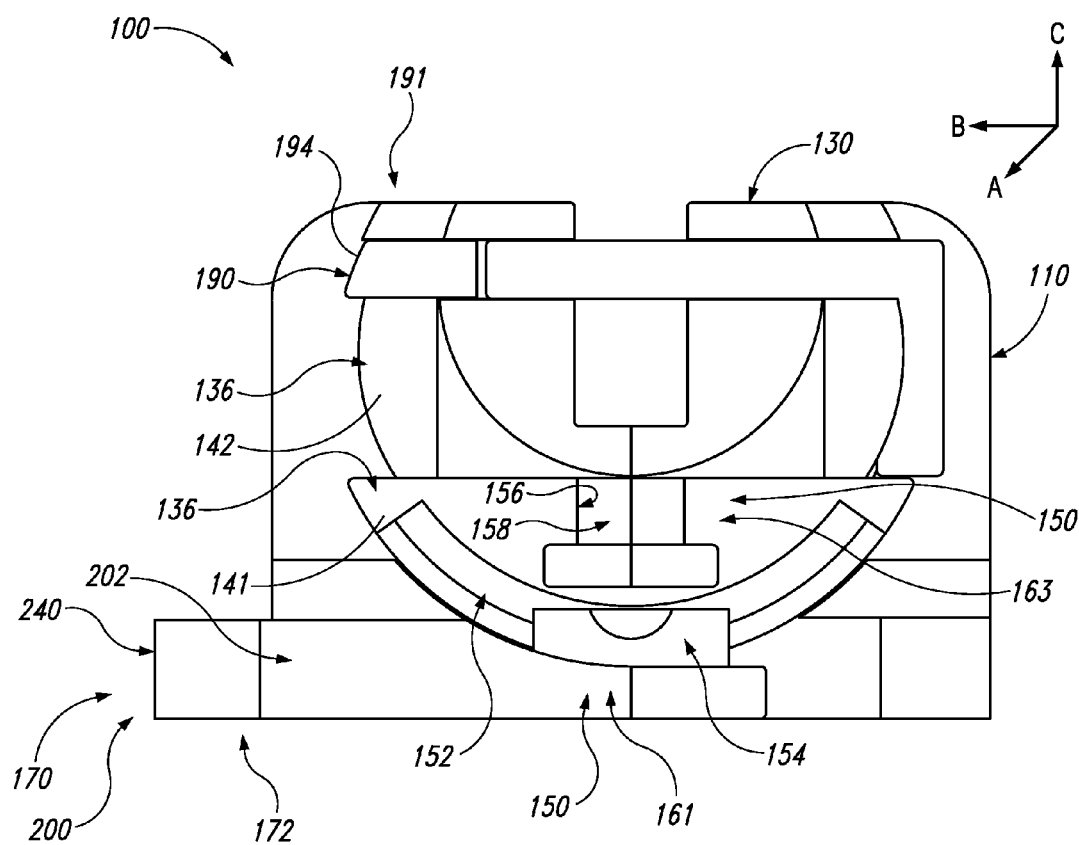
FIG. 13 is a side partial cross-sectional view illustrating an alternative structure for the arcuate core of the orthodontic bracket assembly of FIG. 9.

As illustrated in FIGS. 9-13, assembly 100 may be a self-ligating orthodontic bracket assembly 100 that includes a ligating structure 190. Ligating structure 190 may include a gate 194 that is configured to be selectively transitioned between a closed configuration 191, as illustrated in FIGS. 11 and 13, and an open configuration 193, as illustrated in FIGS. 9-10 and 12.

Sliding retention structure 200 of FIGS. 9-13 includes a sliding wedge 240 that is configured to operatively translate within a sliding retention structure receptacle 202. As indicated in FIGS. 9-10 and 12, sliding wedge 240 may include and/or define a tool-receiving portion 180 that is configured to receive a tool. The tool may be utilized to transition the sliding wedge between an engaged configuration 172, as illustrated in FIGS. 9-11 and 13, and a disengaged configuration 174, as illustrated in FIG. 12.

As perhaps illustrated most clearly in FIG. 12, assembly 100 includes a rotation-directing structure 150. Rotation-directing structure 150 includes a groove 152, which is defined by arcuate core 130, and a post 154, which is defined by bracket body 110 and is configured to be received within groove 152. Groove 152 and post 154 collectively may be utilized to permit rotating of arcuate core 130 about a given rotational axis (such as the A-axis in FIG. 12) while restricting rotation of arcuate core 130 about one or more other axes (such as the B-axis and the C-axis of FIG. 12).

As perhaps illustrated most clearly in FIG. 10, sliding wedge 240 includes a catch 210. Catch 210 may be configured to operatively retain sliding wedge 240 within sliding retention structure receptacle 202 while permitting limited translation of the sliding retention structure within the sliding retention structure receptacle.

FIG. 13 is a schematic view illustrating an alternative structure for arcuate core 130 of the orthodontic bracket assemblies 100 of FIG. 9. In FIG. 13, arcuate core 130 includes a plurality of arcuate core sections 136, including at least a first arcuate core section 141 and a second arcuate core section 142. Assembly 100 of FIG. 13 also includes two rotation-directing structures 150, including at least a first rotation-directing structure 161 and a second rotation-directing structure 163. Similar to assembly 100 of FIGS. 9-12, first rotation-directing structure 161 includes a groove 152 and a post 154 and is configured to permit rotation of first arcuate core section 141 about a first rotational axis (such as the A-axis of FIG. 13) but to resist rotation of the first arcuate core about the B-axis and the C-axis. Second rotation-directing structure 163 includes a hole 156 and a stem 158 and is configured to permit rotation of second arcuate core 142 about the C-axis of FIG. 13 but to resist rotation of the second arcuate core about the A-axis and the B-axis. Thus, first rotation-directing structure 161 and second rotation-directing structure 163 together permit rotation of an archwire slot 132 that is defined by arcuate core 130 about two rotational axes (the A-axis and the C-axis) but restrict rotation of the archwire slot about a third rotational axis (the B-axis).

Figure 14:
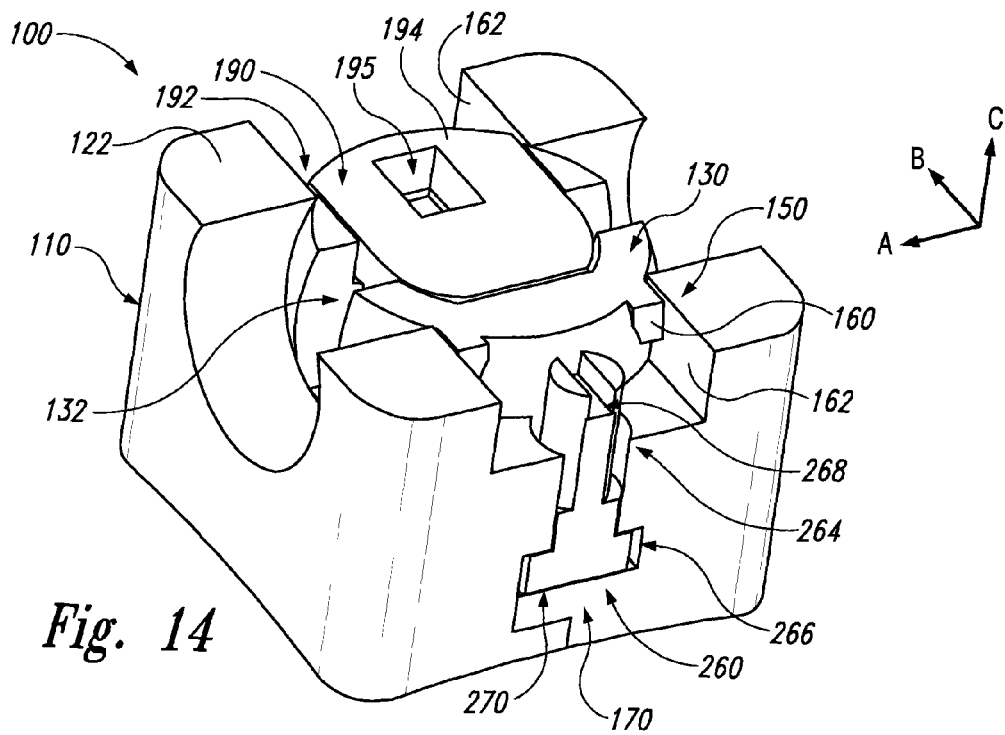
FIG. 14 is a less schematic view of another example of an orthodontic bracket assembly, according to the present disclosure, that includes a bracket body, an arcuate core, and a rotating cam retention structure.
Figure 15:
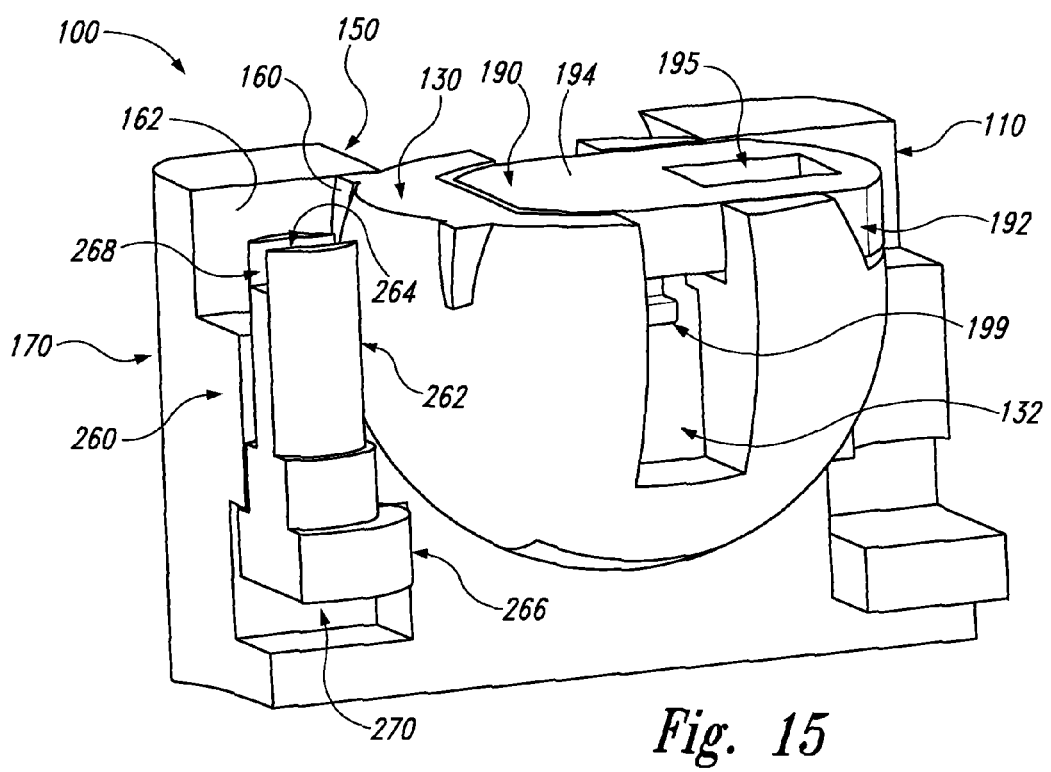
FIG. 15 is a fragmentary view of a portion of the orthodontic bracket assembly of FIG. 14.
Figure 16:
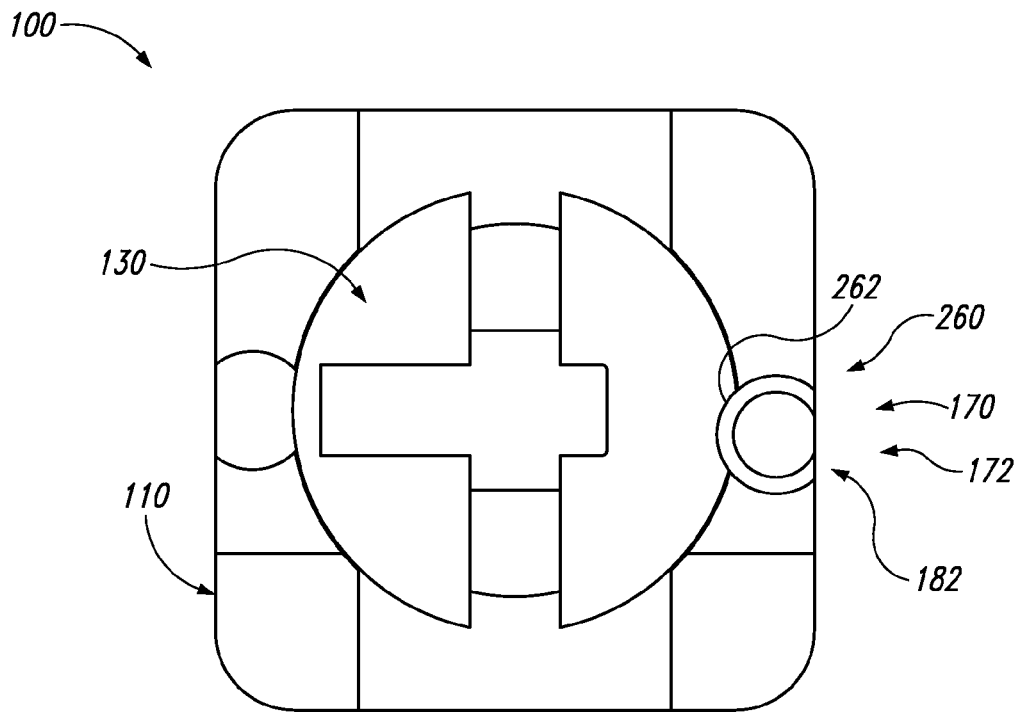
FIG. 16 is a top-down cross-sectional view of the orthodontic bracket assembly of FIG. 14 illustrating the rotating cam retention structure in an engaged configuration.
Figure 17:
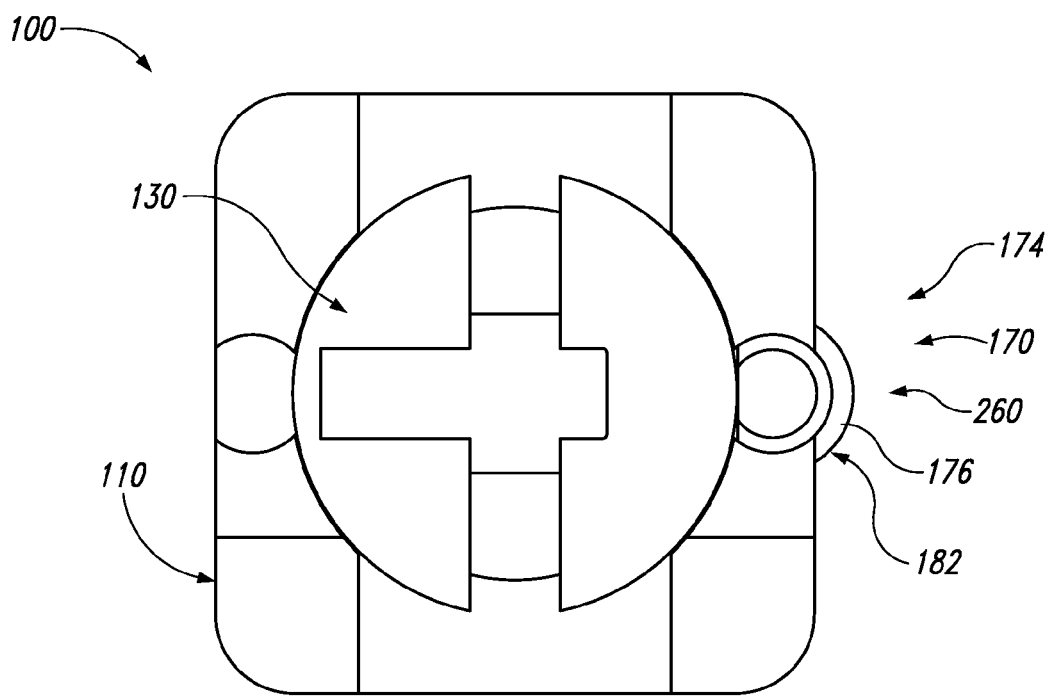
FIG. 17 is a top-down cross-sectional view of the orthodontic bracket assembly of FIG. 14 illustrating the rotating cam retention structure in a disengaged configuration.

FIG. 14 is a less schematic view of another example of an orthodontic bracket assembly 100, according to the present disclosure, that includes a bracket body 110, an arcuate core 130, and a retention structure 170 in the form of a rotating cam retention structure 260. FIG. 15 is a view of a portion of the orthodontic bracket assembly of FIG. 14. FIG. 16 is a top-down cross-sectional view of the orthodontic bracket assembly of FIG. 14 illustrating the rotating cam retention structure in an engaged configuration 172, and FIG. 17 is a top-down cross-sectional view of the orthodontic bracket assembly of FIG. 14 illustrating the rotating cam retention structure in a disengaged configuration 174. Rotating cam retention structure 260 may be oriented at least substantially perpendicular to top 122 of bracket body 110 within assembly 100 and includes an arcuate core-contacting region 262, an actuation region 264, and a retention region 266.

As illustrated in FIG. 16, rotating cam retention structure 260 is shaped to operatively engage arcuate body 130 when the rotating cam retention structure is in engaged configuration 172. Conversely, and as illustrated in FIG. 17, rotating cam retention structure 260 is shaped to provide clearance for rotation of arcuate body 130 when the rotating cam retention structure is in disengaged configuration 174.

Arcuate core-contacting region 262 may be adapted, configured, sized, shaped, and/or located to selectively contact, operatively engage, and/or press against arcuate core 130 when the rotating cam retention structure is in engaged configuration 172, as illustrated in FIG. 16. In addition, arcuate core-contacting region 262 also may be adapted, configured, sized, shaped, and/or located to be spaced apart from arcuate core 130, to not contact arcuate core 130, to not operatively engage arcuate core 130, and/or to not press against arcuate core 130 when the rotating cam retention structure is in disengaged configuration 174, as illustrated in FIG. 17. Additionally or alternatively, arcuate core-contact region 262 may contact, operatively engage, and/or press against arcuate core 130 when the rotating cam retention structure is in the disengaged configuration; however, a contact force therebetween may be insufficient to retain arcuate core 130 at the selected rotational orientation within bracket body 110. Examples of arcuate core-contact region 262 include any suitable surface of rotating cam retention structure 260, such as a lobe, a cam, and/or a D-shaped region that may be defined by the rotating cam retention structure.

Actuation region 264 may be adapted, configured, sized, shaped, and/or located to receive an external force and to transition the rotating cam retention structure between the engaged configuration and the disengaged configuration responsive to receipt of the external force. As an example, and as illustrated in FIGS. 14-15, actuation region 264 may include tool receptacle 268 that may be adapted, configured, sized, and/or shaped to receive an actuation tool. Under these conditions, the actuation tool may be utilized to apply the external force. As another example, actuation region 264 also may include a lever arm that is configured to receive the external force.

Retention region 266 may be adapted, configured, sized, shaped, and/or located to be received within a retention region receptacle 270 that may be defined by bracket body 110. Retention region 266 may be operatively retained within the retention region receptacle such that rotating cam retention structure 260 is operatively retained within assembly 100 and/or within bracket body 110 thereof. In addition, both retention region 266 and retention region receptacle 270 may be sized and/or shaped to permit rotation of rotating cam retention structure 260 when the rotating cam retention structure is transitioned, or to permit the rotating cam retention structure to be transitioned, between the engaged configuration and the disengaged configuration. Examples of retention region 266 include a bearing surface, a (substantially) cylindrical bearing surface, and/or a partially cylindrical bearing surface.

FIGS. 14-17 also provide less schematic examples of structures and/or features of assemblies 100, bracket bodies 110, arcuate cores 130, and/or retention structures 170 according to the present disclosure that are discussed herein with reference to FIGS. 1-4. As an example, FIGS. 14-15 illustrate a ligating structure 190 including a gate 194 and a ligating structure receptacle 192 that is configured to receive the gate. Gate 194 includes a biasing mechanism 199, which is shown in FIG. 15. As yet another example, gate 194 includes a ligating structure tool-receiving portion 195.

As another example, arcuate core 130 includes a rotation-directing structure 150 in the form of a plurality of ribs 160. Ribs 160 are located, sized, and/or shaped to be directed by guiding surface 162 to permit restricted rotation of arcuate core 130 about the A-axis of FIG. 14 and to restrict rotation of arcuate core 130 about the B-axis and/or the C-axis.

As yet another example, rotating cam retention structure 260 of FIGS. 14-17 includes an indicator 176, as illustrated in FIG. 17. Indicator 176 is shaped to project from bracket body 110 when rotating cam retention structure 260 is in disengaged configuration 174 and to be received within an indicator recess 182 when the rotating cam retention structure is in engaged configuration 172, as illustrated in FIG. 16.

Figure 18:
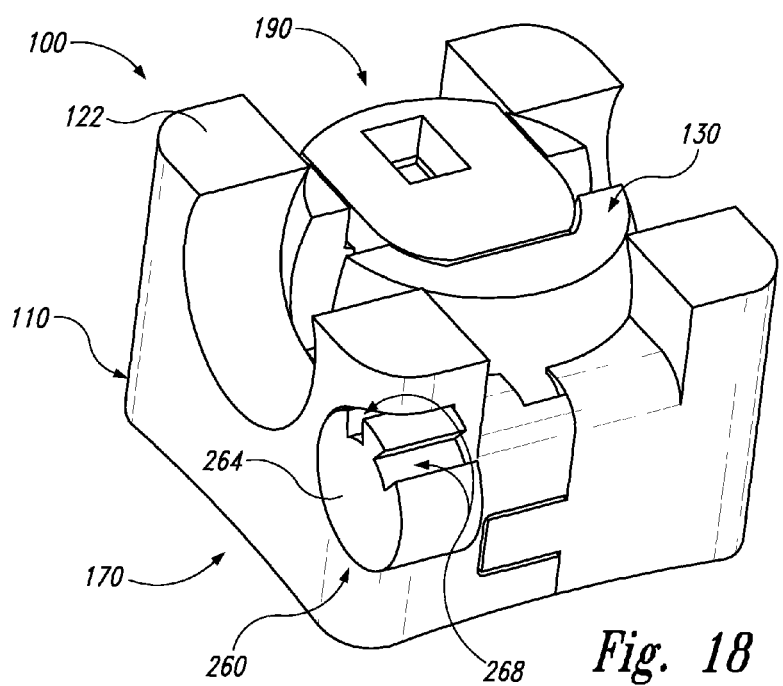
FIG. 18 is a less schematic view of another example of an orthodontic bracket assembly, according to the present disclosure, that includes a bracket body, an arcuate core, and a rotating cam retention structure.
Figure 19:
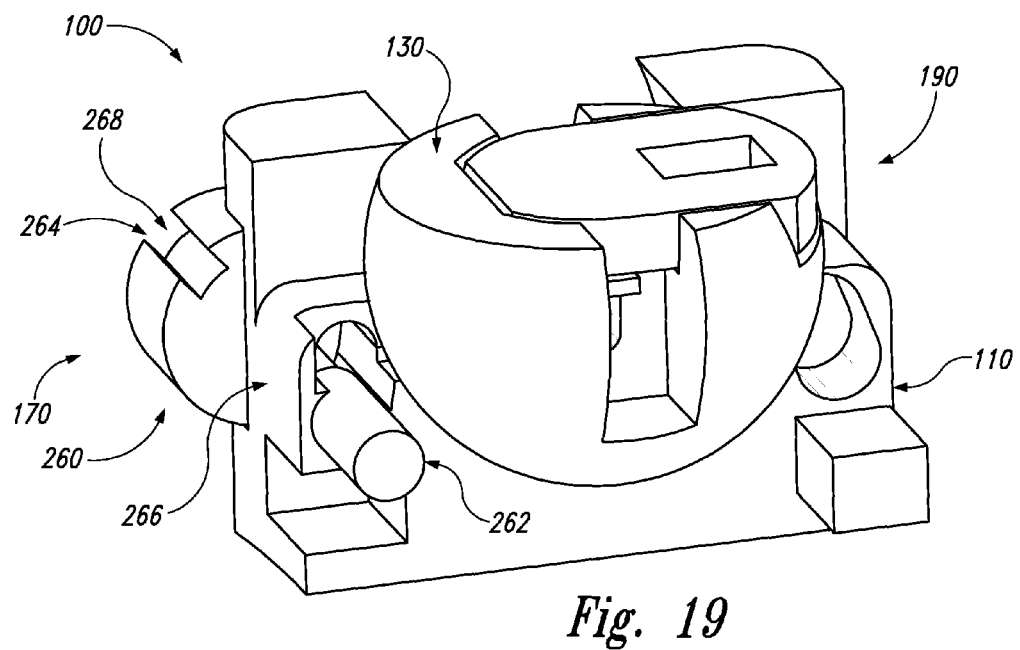
FIG. 19 is a fragmentary view of a portion of the orthodontic bracket assembly of FIG. 18.
Figure 20:
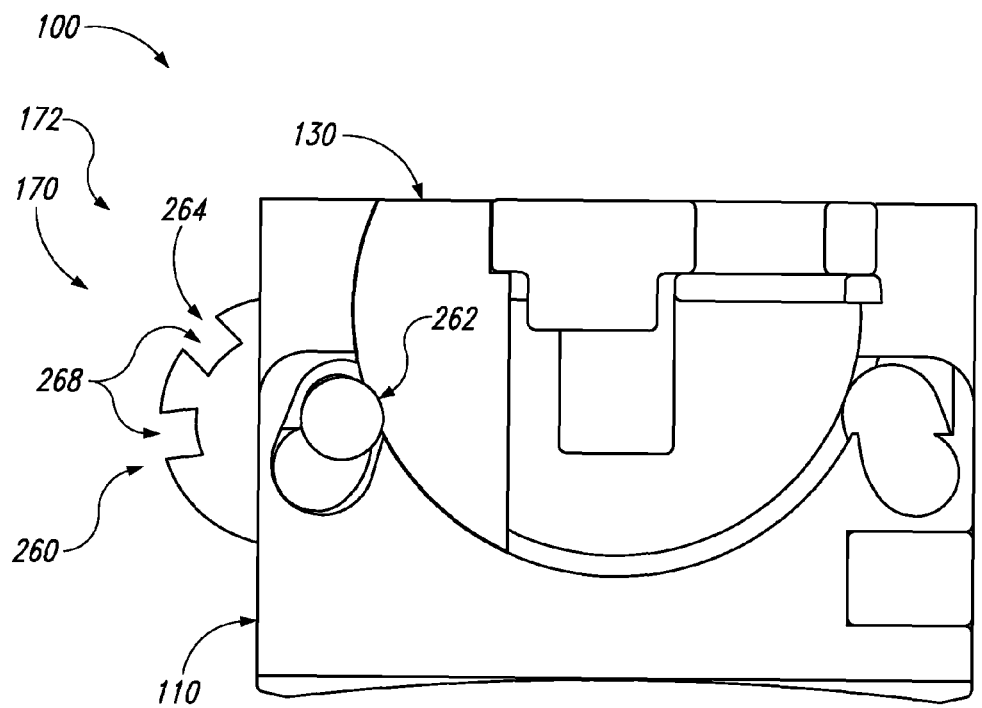
FIG. 20 is a fragmentary side view of a portion of the orthodontic bracket assembly of FIG. 18 illustrating the rotating cam retention structure in an engaged configuration.
Figure 21:
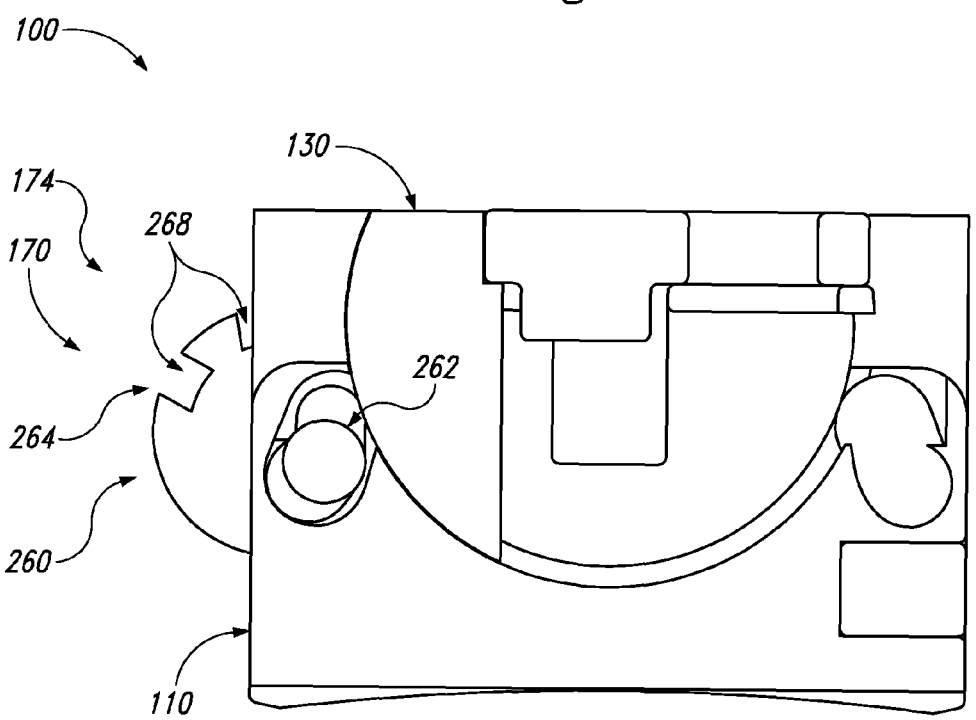
FIG. 21 is a fragmentary side view of a portion of the orthodontic bracket assembly of FIG. 18 illustrating the rotating cam retention structure in a disengaged configuration.

FIG. 18 is a less schematic view of another example of an orthodontic bracket assembly 100, according to the present disclosure, that includes a bracket body 110, an arcuate core 130, and a retention structure 170 in the form of a rotating cam retention structure 260. FIG. 19 is a view of a portion of the orthodontic bracket assembly of FIG. 18. FIG. 20 is a side view of a portion of the orthodontic bracket assembly of FIG. 18 illustrating the rotating cam retention structure in an engaged configuration 172. FIG. 21 is a side view of a portion of the orthodontic bracket assembly of FIG. 18 illustrating the rotating cam retention structure in a disengaged configuration 174. Rotating cam retention structure 260 may be oriented at least substantially parallel to top 122 of bracket body 110 within assembly 100 and includes a core-contacting region 262, an actuation region 264, and a retention region 266.

In FIGS. 18-21, rotating cam retention structure 260 may be shaped to operatively translate core-contacting region 262 between engaged configuration 172, as illustrated in FIG. 20, and disengaged configuration 174, as illustrated in FIG. 21, responsive to rotation of actuation region 264. As an example, and as illustrated in FIGS. 20-21, core-contacting region 262 may be acentric with actuation region 264 such that rotation of actuation region 264 produces translation of core-contacting region 262 relative to arcuate body 130, into contact with arcuate body 130, out of contact with arcuate body 130, and/or between the engaged configuration and the disengaged configuration.

Figure 22:
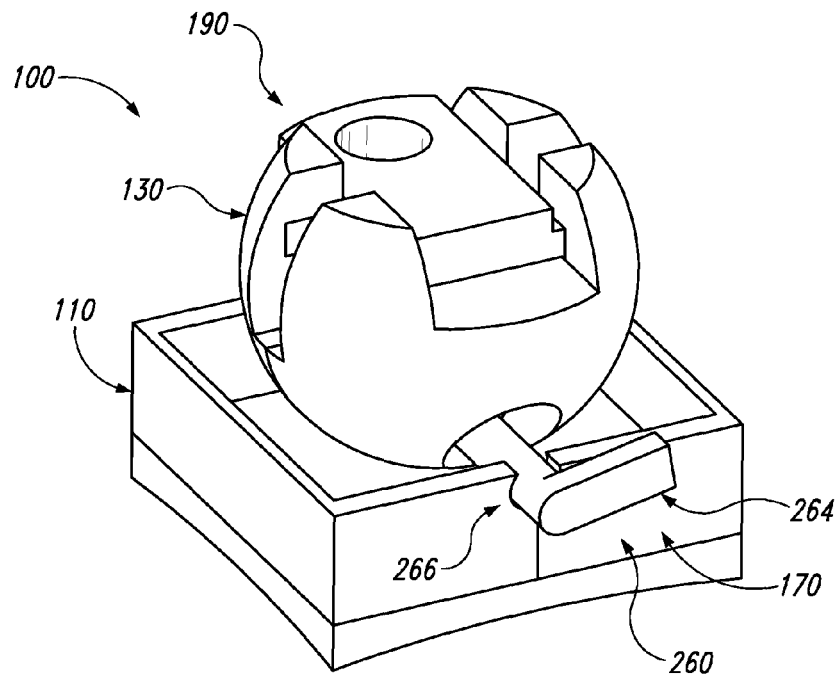
FIG. 22 is a fragmentary less schematic view of another example of an orthodontic bracket assembly, according to the present disclosure, that includes a bracket body, an arcuate core, and a rotating cam retention structure.
Figure 23:
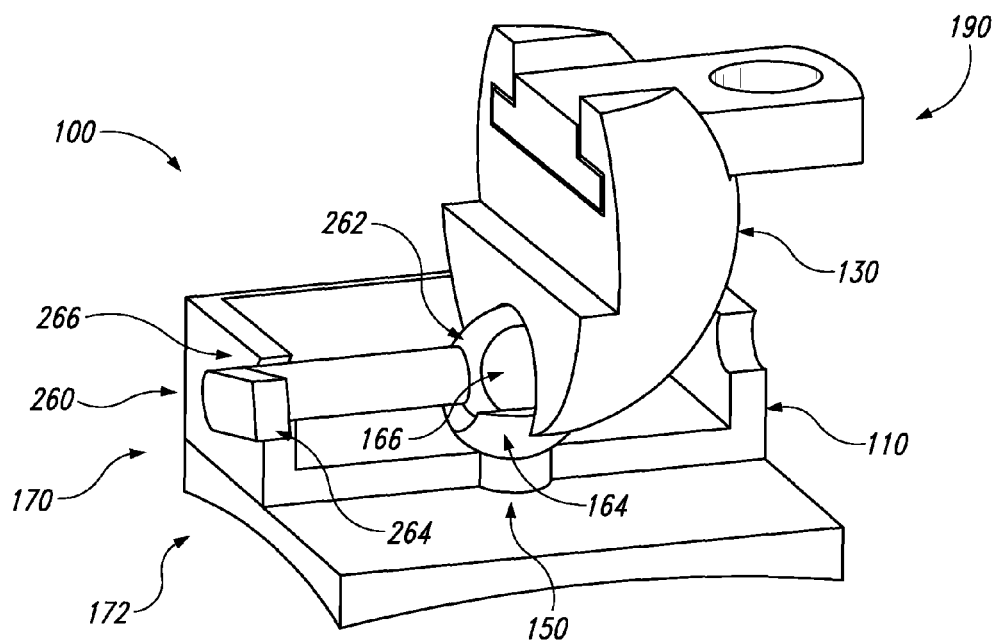
FIG. 23 is a fragmentary view of a portion of the orthodontic bracket assembly of FIG. 22.
Figure 24:
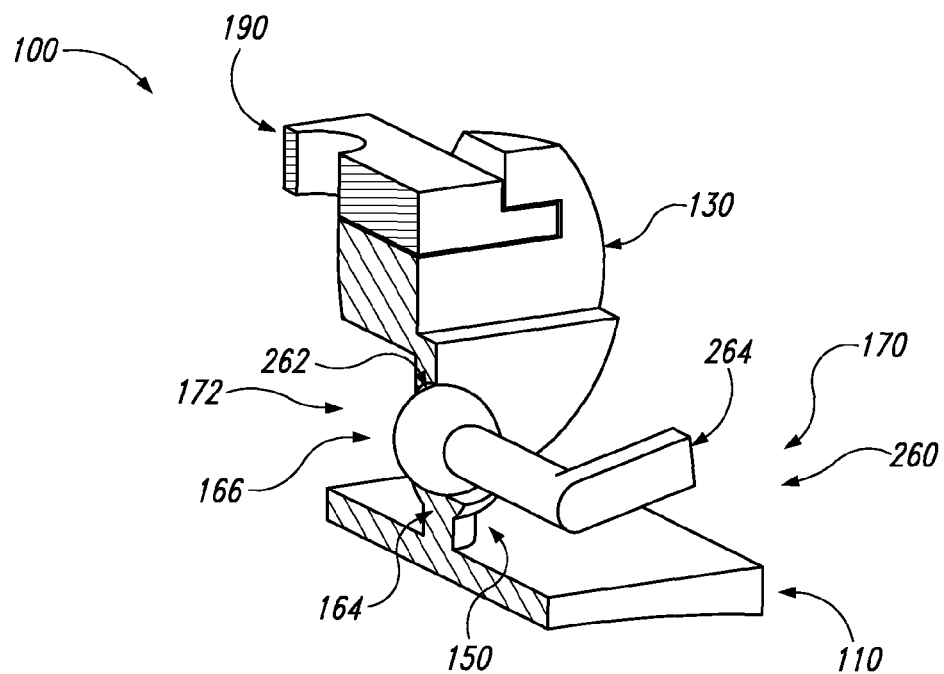
FIG. 24 is a fragmentary cross-sectional side view of a portion of the orthodontic bracket assembly of FIG. 22 illustrating the rotating cam retention structure in an engaged configuration.
Figure 25:
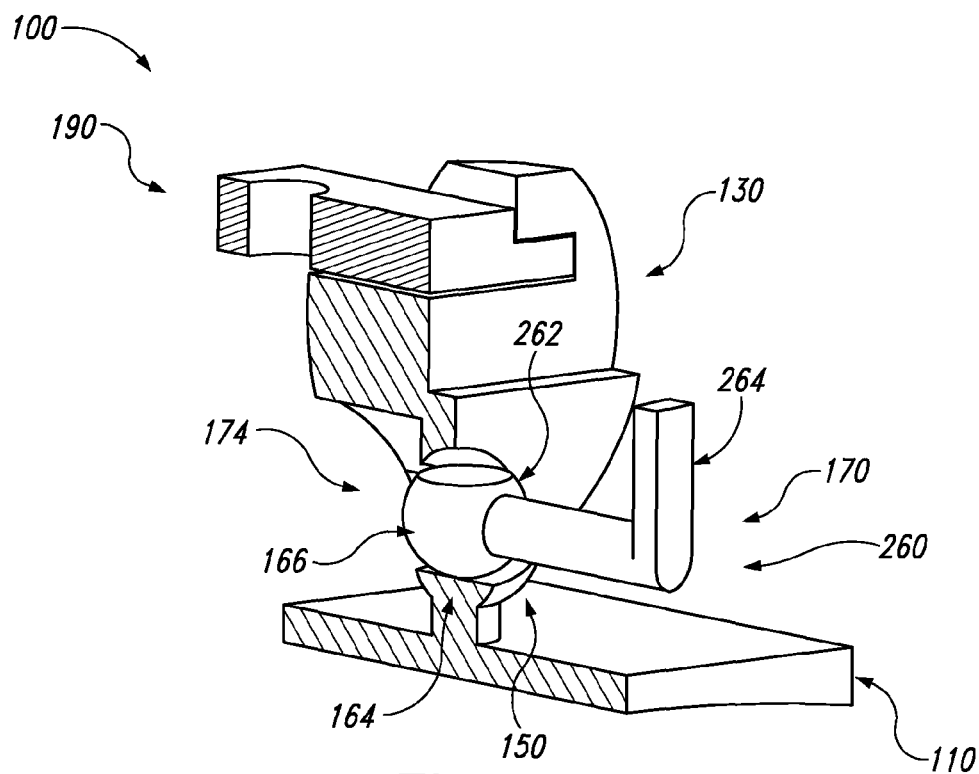
FIG. 25 is a fragmentary cross-sectional side view of a portion of the orthodontic bracket assembly of FIG. 22 illustrating the rotating cam retention structure in a disengaged configuration.

FIG. 22 is a less schematic view of another example of an orthodontic bracket assembly 100, according to the present disclosure, that includes a bracket body 110, an arcuate core 130, and a retention structure 170 in the form of a rotating cam retention structure 260. FIG. 23 is a view of a portion of the orthodontic bracket assembly of FIG. 22. FIG. 24 is a cross-sectional side view of a portion of the orthodontic bracket assembly of FIG. 22 illustrating the rotating cam retention structure in an engaged configuration 172. FIG. 25 is a cross-sectional side view of a portion of the orthodontic bracket assembly of FIG. 22 illustrating the rotating cam retention structure in a disengaged configuration 174.

Similar to rotating cam retention structures 260 of FIGS. 14-21, rotating cam retention structure 260 of FIGS. 22-25 includes an arcuate core-contacting region 262 (labelled in FIGS. 23-25), an actuation region 264, and a retention region 266 (labelled in FIGS. 22-23). In FIGS. 22-25, actuation region 264 may include and/or be a lever arm that extends from rotating cam retention structure 260. In addition, arcuate core-contacting region 262 may include and/or be a partial sphere that is shaped to operatively engage arcuate core 130 when the rotating cam is in the engaged configuration (as illustrated in FIG. 24) and to provide clearance for rotation of the arcuate core relative to bracket body 110 when the rotating cam is in the disengaged configuration (as illustrated in FIG. 25).

As perhaps illustrated most clearly in FIG. 23, assembly 100 of FIGS. 22-25 also may include a rotation-directing structure 150. Rotation-directing structure 150 may include a partial ball 164 and a socket 166 that is shaped to receive the partial ball. Such a rotation-directing structure 150 may permit limited rotation of arcuate core 130 relative to bracket body 110 in any given direction when the rotating cam retention structure is in the disengaged configuration and restricting rotation of the arcuate core relative to the bracket body when the rotating cam retention structure is in the engaged configuration. As an example, and when the rotating cam retention structure is in the engaged configuration of FIG. 24, the rotating cam retention structure presses arcuate core 130 away from bracket body 110, thereby frictionally engaging ball 164 and socket 166 and restricting rotation of the arcuate core relative to the bracket body. Conversely, and when the rotating cam retention structure is in the disengaged configuration of FIG. 25, the illustrated clearance between arcuate core-contacting region 262 and arcuate core 130 decreases and/or eliminates the frictional engagement between ball 164 and socket 166, thereby permitting rotation of the arcuate core relative to the bracket body.

FIGS. 5-25 illustrate bracket bodies 110 and/or arcuate cores 130 that generally are formed from two symmetrical halves. While such a construction is not required of all embodiments, the symmetry of the halves of bracket bodies 110 and/or of arcuate cores 130 may improve manufacturability of the various components of assemblies 100, may decrease manufacturing costs of assemblies 100, may provide for easier assembly of assemblies 100, and/or may simplify utilization of assemblies 100 to provide selected and/or desired prescriptive forces to a tooth to which the orthodontic bracket assemblies may be operatively affixed.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B")

may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

As used herein, the phrase, "for example," the phrase, "as an example," and/or simply the term "example," when used with reference to one or more components, features, details, structures, and/or embodiments according to the present disclosure, are intended to convey that the described component, feature, detail, structure, and/or embodiment is an example of components, features, details, structures, and/or embodiments according to the present disclosure. Thus, the described component, feature, detail, structure, and/or embodiment is not intended to be limiting, required, or exclusive/exhaustive; and other components, features, details, structures, and/or embodiments, including structurally and/or functionally similar and/or equivalent components, features, details, structures, and/or embodiments, are also within the scope of the present disclosure.

Examples of adjustable-prescription orthodontic brackets according to the present disclosure are presented in the following enumerated paragraphs.

A1. An orthodontic bracket assembly, comprising:
a bracket body that defines an arcuate receptacle, wherein the bracket body includes a base, which is configured to be proximal a tooth, and an opposed top, which is configured to be distal the tooth, and further wherein the arcuate receptacle extends toward the base from the top;
an arcuate core that is received within the arcuate receptacle and that defines an archwire slot sized to receive an archwire, wherein the arcuate receptacle is shaped to retain the arcuate core therein and to permit rotation of the arcuate core therein; and
a sliding retention structure that is configured to selectively retain the arcuate core at a selected rotational orientation within the bracket body, wherein the sliding retention structure is configured to be selectively translated between a disengaged configuration, in which the sliding retention structure permits rotation of the arcuate core relative to the bracket body, and an engaged configuration, in which the sliding retention structure retains, and optionally frictionally retains, the arcuate core at the selected rotational orientation, and further wherein the sliding retention structure extends at least partially between the bracket body and the arcuate core at least when the sliding retention structure is in the engaged configuration.

A2. The assembly of paragraph A1, wherein the sliding retention structure extends between the base and the arcuate core.

A3. The assembly of any of paragraphs A1-A2, wherein the sliding retention structure is spaced apart from the archwire slot.

A4. The assembly of any of paragraphs A1-A3, wherein the arcuate core extends between the sliding retention structure and the archwire slot.

A5. The assembly of any of paragraphs A1-A4, wherein the sliding retention structure extends at least partially between the bracket body and the arcuate core when the sliding retention structure is in the disengaged configuration.

A6. The assembly of any of paragraphs A1-A5, wherein the sliding retention structure is configured to translate within a sliding retention structure receptacle to transition between the engaged configuration and the disengaged configuration.

A7. The assembly of any of paragraphs A1-A6, wherein the sliding retention structure is configured to operatively engage the arcuate core with the bracket body to retain the arcuate core at the selected rotational orientation.

A8. The assembly of any of paragraphs A1-A7, wherein the sliding retention structure is configured to urge the arcuate core against the bracket body to retain the arcuate core at the selected rotational orientation.

A9. The assembly of any of paragraphs A1-A8, wherein the sliding retention structure is configured to interlock the arcuate core with the bracket body to retain the arcuate core at the selected rotational orientation.

A10. The assembly of any of paragraphs A1-A9, wherein the sliding retention structure includes a contact region configured to receive a portion of the arcuate core when the sliding retention structure is in the engaged configuration.

A11. The assembly of paragraph A10, wherein the contact region includes a concave surface profile, optionally wherein a radius of the concave surface profile corresponds to, or equals, a radius of the portion of the arcuate core that contacts the contact region.

A12. The assembly of any of paragraphs A10-A11, wherein the contact region includes a hole in the sliding retention structure, wherein a radius of the hole is less than a/the radius of the portion of the arcuate core that is received within the hole such that the contact region is a (substantially) circular, or arcuate, line contact about a perimeter of the hole.

A13. The assembly of any of paragraphs A10-A12, wherein the contact region includes a friction-enhancing region configured to increase a frictional force between the arcuate core and the sliding retention structure.

A14. The assembly of paragraph A13, wherein the friction-enhancing region includes at least one of a roughened region, a resilient material, a resilient gasket, and a resilient O-ring.

A15. The assembly of any of paragraphs A1-A14, wherein the assembly defines a sliding retention structure receptacle that is configured to receive the sliding retention structure.

A16. The assembly of paragraph A15, wherein the sliding retention structure includes a catch shaped to retain the sliding retention structure within the sliding retention structure receptacle of the bracket body.

A17. The assembly of any of paragraphs A15-A16, wherein the sliding retention structure receptacle is at least partially defined by at least one, optionally at least two, and further optionally all of the bracket body, the arcuate core, and the base.

A18. The assembly of any of paragraphs A15-A17, wherein, when the sliding retention structure is present within the sliding retention structure receptacle, the sliding retention structure is compressed between the arcuate core and one of the bracket body and the base to retain the arcuate core at the selected rotational orientation.

A19. The assembly of any of paragraphs A15-A18, wherein, when the sliding retention structure is present within the sliding retention structure receptacle, the sliding retention structure generates an interference fit between the arcuate core and the bracket body.

A20. The assembly of any of paragraphs A15-A19, wherein, when the sliding retention structure is present within the sliding retention structure receptacle, the sliding retention structure generates an interference fit between the sliding retention structure and the arcuate core.

A21. The assembly of any of paragraphs A1-A20, wherein the sliding retention structure includes a sliding spring.

A22. The assembly of paragraph A21, wherein the sliding spring includes at least one of a sliding clip, a sliding torsion spring, and a sliding flat spring.

A23. The assembly of any of paragraphs A21-A22, wherein the sliding spring has an arcuate shape.

A24. The assembly of any of paragraphs A21-A23, wherein the sliding spring has a relief region shaped to provide clearance for rotation of the arcuate core when the sliding spring is in the disengaged configuration.

A25. The assembly of paragraph A24, wherein the bracket body includes a detent shaped to receive the relief region when the sliding spring is in the disengaged configuration.

A26. The assembly of paragraph A25, wherein the relief region and the detent together are shaped to bias the sliding spring toward the disengaged configuration when the relief region is received within the detent.

A27. The assembly of any of paragraphs A25-A26, wherein the sliding spring is biased to automatically transition to the engaged configuration when the relief region is urged from the detent.

A28. The assembly of any of paragraphs A21-A27, wherein the sliding spring is biased to remain in the engaged configuration unless urged from the engaged configuration.

A29. The assembly of any of paragraphs A21-A28, wherein the sliding spring includes a bias region that is shaped to retain the sliding spring in the engaged configuration unless urged from the engaged configuration.

A30. The assembly of paragraph A29, wherein the bracket body includes a transition structure, wherein the transition structure and the bias region together are shaped to bias the sliding spring toward the engaged configuration.

A31. The assembly of any of paragraphs A21-A30, wherein the sliding spring is configured to deform upon transitioning between the engaged configuration and the disengaged configuration, optionally wherein the sliding spring includes a deformation region configured to deform upon transitioning between the engaged configuration and the disengaged configuration.

A32. The assembly of any of paragraphs A21-A31, wherein the sliding spring is a metallic sliding spring, optionally wherein the sliding spring is formed from a nickel-titanium alloy.

A33. The assembly of any of paragraphs A1-A32, wherein the sliding retention structure includes a sliding wedge.

B1. An orthodontic bracket assembly, comprising:
a bracket body that defines an arcuate receptacle, wherein the bracket body includes a base, which is configured to be proximal a tooth, and an opposed top, which is configured to be distal the tooth, and further wherein the arcuate receptacle extends toward the base from the top;
an arcuate core that is received within the arcuate receptacle and that defines an archwire slot sized to receive an archwire, wherein the arcuate receptacle is shaped to retain the arcuate core therein and to permit rotation of the arcuate core therein; and
a rotating cam retention structure that is configured to selectively retain the arcuate core at a selected rotational orientation relative to the bracket body, wherein the rotating cam retention structure is configured to be selectively rotated between a disengaged configuration, in which the rotating cam retention structure permits rotation of the arcuate core relative to the bracket body, and an engaged configuration, in which the rotating cam retention structure retains, and optionally frictionally retains, the arcuate core at the selected rotational orientation.

B2. The assembly of paragraph B1, wherein the rotating cam retention structure includes:
(i) an arcuate core-contacting region configured to selectively contact the arcuate core when the rotating cam retention structure is in the engaged configuration;
(ii) an actuation region configured to receive an external force and to transition the rotating cam retention structure between the disengaged configuration and the engaged configuration responsive to receipt of the external force; and
(iii) a retention region shaped to be received within a retention region receptacle that is defined by the bracket body, to retain the rotating cam retention structure within the orthodontic bracket assembly, and to permit rotation of the rotating cam retention structure when the rotating cam retention structure is transitioned between the engaged configuration and the disengaged configuration.

B3. The assembly of paragraph B2, wherein the arcuate core-contacting region includes a lobe.

B4. The assembly of any of paragraphs B2-B3, wherein the arcuate core-contacting region includes a cam.

B5. The assembly of any of paragraphs B2-B4, wherein the actuation region includes a tool receptacle configured to receive an actuation tool, wherein the tool is configured to apply the external force.

B6. The assembly of any of paragraphs B2-B5, wherein the actuation region includes a lever arm.

B7. The assembly of any of paragraphs B2-B6, wherein the retention region includes a (substantially) cylindrical bearing surface.

C1. The assembly of any of paragraphs A1-B7, wherein the arcuate receptacle has a shape that corresponds to a shape of a portion of the arcuate core that contacts the bracket body.

C2. The assembly of paragraph C1, wherein the portion of the arcuate core defines a partial cylinder.

C3. The assembly of paragraph C1, wherein the portion of the arcuate core defines a partial sphere.

C4. The assembly of any of paragraphs A1-C3, wherein the base is configured to be operatively affixed to a tooth.

C5. The assembly of paragraph C4, wherein a remainder of the bracket body is at least one of adhered, melted, welded, and brazed to the base.

C6. The assembly of any of paragraphs A1-05, wherein the assembly further includes a ligating structure that is operatively affixed to the arcuate core and configured to selectively retain an archwire within the archwire slot, optionally wherein the orthodontic bracket assembly is a self-ligating orthodontic bracket assembly.

C7. The assembly of paragraph C6, wherein the ligating structure defines a closed configuration, in which the ligating structure retains the archwire within the archwire slot, and an open configuration, in which the ligating structure does not retain the archwire within the archwire slot.

C8. The assembly of paragraph C7, wherein the assembly further includes a ligating structure receptacle that is configured to receive the ligating structure.

C9. The assembly of paragraph C8, wherein the ligating structure is configured to translate within the ligating structure receptacle to transition between the closed configuration and the open configuration.

C10. The assembly of any of paragraphs C6-C9, wherein the ligating structure is an active ligating structure, optionally wherein the active ligating structure includes a biasing mechanism that is configured to provide a compressive force to the archwire.

C11. The assembly of any of paragraphs C6-C9, wherein the ligating structure is a passive ligating structure.

C12. The assembly of any of paragraphs A1-C11, wherein the assembly further includes a ligature-receiving structure configured to receive a ligature.

C13. The assembly of any of paragraphs A1-C12, wherein the assembly includes a rotation-directing structure configured to permit rotation of the arcuate core about a rotational axis and to limit rotation of the arcuate core about another axis that is different from the rotational axis.

C14. The assembly of paragraph C13, wherein the rotational axis extends at least substantially in one of a gingival-occlusal direction, a mesial-distal direction, a buccal-lingual direction, and a labial-lingual direction.

C15. The assembly of any of paragraphs C13-C14, wherein the rotation-directing structure includes a groove and a post that is configured to translate within the groove.

C16. The assembly of paragraph C15, wherein one of the groove and the post is defined by the arcuate core.

C17. The assembly of paragraph C16, wherein the other of the groove and the post is defined by one of the bracket body and the base.

C18. The assembly of any of paragraphs C13-C17, wherein the rotation-directing structure includes a hole and a stem that is configured to rotate within the hole.

C19. The assembly of paragraph C18, wherein one of the hole and the stem is defined by the arcuate core.

C20. The assembly of paragraph C19, wherein the other of the hole and the stem is defined by one of the bracket body and the base.

C21. The assembly of any of paragraphs C13-C20, wherein the rotation-directing structure includes a rib that projects from the arcuate core.

C22. The assembly of any of paragraphs C13-C21, wherein the rotation-directing structure is a first rotation-directing structure, wherein the rotational axis is a first rotational axis, and further wherein the assembly includes a second rotation-directing structure that is configured to permit rotation of the arcuate core about a second rotational axis.

C23. The assembly of paragraph C22, wherein the second rotational axis is different from the first rotational axis.

C24. The assembly of any of paragraphs C22-C23, wherein the second rotational axis is at least substantially perpendicular to the first rotational axis.

C25. The assembly of paragraph A24, wherein the arcuate core includes a first core section and a second core section, and further wherein the second rotation-directing structure is at least partially defined by the first core section and by the second core section.

C26. The assembly of paragraph C25, wherein the rotation-directing structure is configured to permit rotation of the first core section relative to the second core section.

C27. The assembly of any of paragraphs C22-C26, wherein the retention structure is a first retention structure, wherein the selected rotational orientation is a first selected rotational orientation, and further wherein the assembly further includes a second retention structure configured to selectively retain the arcuate core at a second selected rotational orientation about the second rotational axis.

C28. The assembly of any of paragraphs A1-C27, wherein the arcuate core defines an arcuate core recess configured to receive an arcuate core adjustment tool that is configured to rotate the arcuate core to the selected rotational orientation.

C29. The assembly of any of paragraphs A1-C28, wherein the bracket body is a monolithic structure.

C30. The assembly of any of paragraphs A1-C29, wherein the bracket body includes a first bracket section and a second bracket section, wherein the first bracket section and the second bracket section are operatively affixed to one another, optionally wherein the first bracket section and the second bracket section together define the base, and further optionally wherein the first bracket section and the second bracket section are operatively affixed to a base section that defines the base.

C31. The assembly of any of paragraphs A1-C30, wherein at least one, and optionally both, of the bracket body and the arcuate core includes a friction-enhancing region configured to increase a frictional force between the bracket body and the arcuate core when the retention structure is in the engaged configuration.

C32. The assembly of paragraph C31, wherein the friction-enhancing region includes at least one of a roughened region, a high-friction region, and a resilient material.

C33. The assembly of any of paragraphs A1-C32, wherein the retention structure includes an indicator that projects from the bracket body when the retention structure is in the disengaged configuration, wherein the bracket body defines an indicator recess, and further wherein the indicator is located within the indicator recess when the retention structure is in the engaged configuration.

C34. The assembly of any of paragraphs A1-C33, wherein the retention structure defines a projecting portion, which is shaped to be received within a/the retention structure receptacle, and a tool-receiving portion, which is shaped to receive a tool.

C35. The assembly of paragraph C34, wherein the tool is configured to be received within the tool-receiving portion to transition the retention structure between the engaged configuration and the disengaged configuration.

C36. The assembly of paragraph C35, wherein the tool is configured to be translated to transition the retention structure between the engaged configuration and the disengaged configuration.

C37. The assembly of any of paragraphs C34-C35, wherein the tool is configured to be rotated to transition the retention structure between the engaged configuration and the disengaged configuration.

C38. The assembly of any of paragraphs C34-C37, wherein the assembly further defines an assembly tool-engaging portion that is configured to operatively engage the tool when the retention structure is transitioned between the engaged configuration and the disengaged configuration, optionally wherein the assembly tool-engaging portion is defined by at least one of the base, the bracket body, and the arcuate core.

INDUSTRIAL APPLICABILITY

The assemblies disclosed herein are applicable to the dental and orthodontics industries.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. An orthodontic bracket assembly, comprising:
a bracket body that defines an arcuate receptacle, wherein the bracket body includes a base, which is configured to be proximal a tooth, and an opposed top, which is configured to be distal the tooth, and further wherein the arcuate receptacle extends toward the base from the top;
an arcuate core that is received within the arcuate receptacle and that defines an archwire slot sized to receive an archwire, wherein the arcuate receptacle is shaped to retain the arcuate core therein and to permit rotation of the arcuate core therein; and
a sliding retention structure that is configured to selectively retain the arcuate core at a selected rotational orientation within the bracket body, wherein the sliding retention structure is configured to be selectively translated between a disengaged configuration, in which the sliding retention structure permits rotation of the arcuate core relative to the bracket body, and an engaged configuration, in which the sliding retention structure retains the arcuate core at the selected rotational orientation, and further wherein the sliding retention structure extends at least partially between the bracket body and the arcuate core at least when the sliding retention structure is in the engaged configuration.

2. The assembly of claim 1, wherein the sliding retention structure extends between the base and the arcuate core.

3. The assembly of claim 1, wherein the sliding retention structure is spaced apart from the archwire slot.

4. The assembly of claim 1, wherein the sliding retention structure includes a contact region configured to receive a portion of the arcuate core when the sliding retention structure is in the engaged configuration.

5. The assembly of claim 4, wherein the contact region includes a concave surface profile.

6. The assembly of claim 4, wherein the contact region includes a hole in the sliding retention structure, wherein a radius of the hole is less than a radius of the portion of the arcuate core that is received within the hole.

7. The assembly of claim 4, wherein the contact region includes a friction-enhancing region configured to increase a frictional force between the arcuate core and the sliding retention structure.

8. The assembly of claim 7, wherein the friction-enhancing region includes at least one of a roughened region, a resilient material, a resilient gasket, and a resilient O-ring.

9. The assembly of claim 1, wherein the assembly defines a sliding retention structure receptacle that is configured to receive the sliding retention structure.

10. The assembly of claim 9, wherein the sliding retention structure includes a catch shaped to retain the sliding retention structure within the sliding retention structure receptacle of the bracket body.

11. The assembly of claim 9, wherein, when the sliding retention structure is present within the sliding retention structure receptacle, the sliding retention structure is compressed between the arcuate core and one of the bracket body and the base to retain the arcuate core at the selected rotational orientation.

12. The assembly of claim 1, wherein the sliding retention structure includes a sliding spring.

13. The assembly of claim 12, wherein the sliding spring has a relief region shaped to provide clearance for rotation of the arcuate core when the sliding spring is in the disengaged configuration.

14. The assembly of claim 13, wherein the bracket body includes a detent shaped to receive the relief region when the sliding spring is in the disengaged configuration.

15. The assembly of claim 14, wherein the relief region and the detent together are shaped to bias the sliding spring toward the disengaged configuration when the relief region is received within the detent.

16. The assembly of claim 14, wherein the sliding spring is biased to automatically transition to the engaged configuration when the relief region is urged from the detent.

17. The assembly of claim 12, wherein the sliding spring is biased to remain in the engaged configuration unless urged from the engaged configuration.

18. The assembly of claim 1, wherein the sliding retention structure includes a sliding wedge.

19. The assembly of claim 1, wherein the assembly includes a rotation-directing structure configured to permit rotation of the arcuate core about a rotational axis and to limit rotation of the arcuate core about another axis that is different from the rotational axis.

20. The assembly of claim 1, wherein the sliding retention structure includes an indicator that projects from the bracket body when the sliding retention structure is in the disengaged configuration, wherein the bracket body defines an indicator recess, and further wherein the indicator is located within the indicator recess when the sliding retention structure is in the engaged configuration.

21. The assembly of claim 1, wherein the sliding retention structure frictionally retains the arcuate core at the selected rotational orientation.

22. An orthodontic bracket assembly, comprising:
 a bracket body that defines an arcuate receptacle, wherein the bracket body includes a base, which is configured to be proximal a tooth, and an opposed top, which is configured to be distal the tooth, and further wherein the arcuate receptacle extends toward the base from the top;
 an arcuate core that is received within the arcuate receptacle and that defines an archwire slot sized to receive an archwire, wherein the arcuate receptacle is shaped to retain the arcuate core therein and to permit rotation of the arcuate core therein; and
 a rotating cam retention structure that is configured to selectively retain the arcuate core at a selected rotational orientation relative to the bracket body, wherein the rotating cam retention structure is configured to be selectively rotated between a disengaged configuration, in which the rotating cam retention structure permits rotation of the arcuate core relative to the bracket body, and an engaged configuration, in which the rotating cam retention structure retains the arcuate core at the selected rotational orientation, and further wherein the rotating cam retention structure includes:
  (i) an arcuate core-contacting region configured to selectively contact the arcuate core to retain the arcuate core at the selected rotational orientation when the rotating cam retention structure is in the engaged configuration;
  (ii) an actuation region configured to receive an external force and to transition the rotating cam retention structure between the disengaged configuration and the engaged configuration responsive to receipt of the external force; and
  (iii) a retention region rotationally received within a retention region receptacle defined by the bracket body to retain at least the retention region of the rotating cam retention structure within the retention region receptacle when the rotating cam retention structure is in both the disengaged configuration and the engaged configuration, and to permit rotation of the rotating cam retention structure relative to the bracket body when the rotating cam retention structure is transitioned between the engaged configuration and the disengaged configuration.

23. The assembly of claim 22, wherein the arcuate core-contacting region includes a lobe.

24. The assembly of claim 22, wherein the actuation region includes a tool receptacle configured to receive an actuation tool, wherein the tool is configured to apply the external force.

25. The assembly of claim 22, wherein the actuation region includes a lever arm.

26. The assembly of claim 22, wherein the assembly includes a rotation-directing structure configured to permit rotation of the arcuate core about a rotational axis and to limit rotation of the arcuate core about another axis that is different from the rotational axis.

27. The assembly of claim 22, wherein the rotating cam retention structure includes an indicator that projects from the bracket body when the rotating cam retention structure is in the disengaged configuration, wherein the bracket body defines an indicator recess, and further wherein the indicator is located within the indicator recess when the rotating cam retention structure is in the engaged configuration.

28. The assembly of claim 22, wherein the archwire slot defines a longitudinal axis and includes an opening that extends parallel to the longitudinal axis and is sized to permit an archwire to be selectively inserted into and removed from the archwire slot through the opening, and further wherein in both the disengaged configuration and the engaged configuration, the rotating cam retention structure does not obstruct the opening of the archwire slot.

29. An orthodontic bracket assembly, comprising:
 a bracket body that defines an arcuate receptacle, wherein the bracket body includes a base, which is configured to be proximal a tooth, and an opposed top, which is configured to be distal the tooth, and further wherein the arcuate receptacle extends toward the base from the top;
 an arcuate core that is received within the arcuate receptacle and that defines an archwire slot sized to receive an archwire, wherein the arcuate receptacle is shaped to retain the arcuate core therein and to permit rotation of the arcuate core therein; and
 a retention structure that is configured to selectively retain the arcuate core at a selected rotational orientation within the bracket body, wherein the retention structure is configured to be selectively transitioned between a disengaged configuration, in which the retention structure permits rotation of the arcuate core relative to the bracket body, and an engaged configuration, in which the retention structure retains the arcuate core at the selected rotational orientation; wherein the retention structure extends at least partially between the base and the arcuate core when the retention structure is in the engaged configuration and when the retention structure is in the disengaged configuration; wherein the retention structure is spaced apart from the archwire slot; and further wherein the retention structure does not obstruct the archwire slot in both the disengaged configuration and the engaged configuration.

30. The assembly of claim 29, wherein the retention structure includes a contact region configured to receive a portion of the arcuate core when the retention structure is in the engaged configuration.

31. The assembly of claim 30, wherein the contact region includes a friction-enhancing region configured to increase a frictional force between the arcuate core and the retention structure, and further wherein the friction-enhancing region includes at least one of a roughened region, a resilient material, a resilient gasket, and a resilient O-ring.

32. The assembly of claim 29, wherein the contact region includes a concave surface profile.

33. The assembly of claim 29, wherein the contact region includes a hole in the retention structure, wherein a radius of the hole is less than a radius of the portion of the arcuate core that is received within the hole.

34. The assembly of claim 29, wherein the assembly defines a retention structure receptacle that is configured to receive the retention structure.

35. The assembly of claim 34, wherein the retention structure includes a catch shaped to retain the retention structure within the retention structure receptacle of the bracket body.

36. The assembly of claim 34, wherein, when the retention structure is present within the retention structure receptacle, the retention structure is compressed between the arcuate core and the bracket body to retain the arcuate core at the selected rotational orientation.

37. The assembly of claim 29, wherein the retention structure includes a spring that is resiliently deformed as the retention structure is transitioned between the engaged configuration and the disengaged configuration.

38. The assembly of claim 37, wherein the spring has a relief region shaped to provide clearance for rotation of the arcuate core when the spring is in the disengaged configuration; and further wherein the bracket body includes a detent shaped to receive the relief region when the spring is in the disengaged configuration.

39. The assembly of claim 38, wherein the relief region and the detent together are shaped to bias the spring toward the disengaged configuration when the relief region is received within the detent.

40. The assembly of claim 38, wherein the spring is biased to automatically transition to the engaged configuration when the relief region is urged from the detent.

41. The assembly of claim 37, wherein the spring is biased to remain in the engaged configuration unless urged from the engaged configuration.

42. The assembly of claim 29, wherein the retention structure includes a wedge that is configured to selectively engage the arcuate core to retain the arcuate core in the selected rotational configuration.

43. The assembly of claim 29, wherein the assembly includes a rotation-directing structure configured to permit rotation of the arcuate core about a rotational axis and to limit rotation of the arcuate core about another axis that is different from the rotational axis.

44. The assembly of claim 29, wherein the retention structure includes an indicator that projects from the bracket body when the retention structure is in the disengaged configuration, wherein the bracket body defines an indicator recess, and further wherein the indicator is located within the indicator recess when the retention structure is in the engaged configuration.

45. The assembly of claim 29, wherein the retention structure frictionally retains the arcuate core at the selected rotational orientation.

46. The assembly of claim 29, wherein when transitioning between the disengaged configuration and the engaged configuration, the retention structure is configured to move along at least one of a linear and an arcuate path.

* * * * *